United States Patent
Ehrnsperger et al.

(10) Patent No.: US 12,274,609 B2
(45) Date of Patent: Apr. 15, 2025

(54) ABSORBENT ARTICLE WITH HIGH ABSORBENT MATERIAL CONTENT

(71) Applicant: The Procter & Gamble Company, Cincinnati, OH (US)

(72) Inventors: Bruno Johannes Ehrnsperger, Bad Soden (DE); Blanca Arizti, Frankfurt am Main (DE); Ernesto Bianchi, Oberursel (DE); Hans Adolf Jackels, Mechernich (DE); Carsten Heinrich Kreuzer, Hofheim (DE); Rodrigo Rosati, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 18/526,434

(22) Filed: Dec. 1, 2023

(65) Prior Publication Data
US 2024/0091078 A1    Mar. 21, 2024

Related U.S. Application Data

(63) Continuation of application No. 17/184,762, filed on Feb. 25, 2021, now Pat. No. 12,016,761, which is a
(Continued)

(30) Foreign Application Priority Data

Dec. 10, 2012    (EP) .................................... 12196341

(51) Int. Cl.
*A61F 13/15*    (2006.01)
*A61F 13/475*    (2006.01)
(Continued)

(52) U.S. Cl.
CPC ........ *A61F 13/534* (2013.01); *A61F 13/4753* (2013.01); *A61F 13/49* (2013.01);
(Continued)

(58) Field of Classification Search
CPC .... A61F 13/534; A61F 13/4753; A61F 13/49; A61F 13/49017; A61F 13/5323;
(Continued)

(56) References Cited

U.S. PATENT DOCUMENTS

| 32,649 A | 6/1861 | Rhoades |
| 329,697 A | 11/1885 | Barr |

(Continued)

FOREIGN PATENT DOCUMENTS

| CA | 2308961 A1 | 11/2000 |
| CA | 2593642 A1 | 7/2006 |

(Continued)

OTHER PUBLICATIONS

US 8,293,969 B2, 10/2012, Uchimoto et al. (withdrawn)
(Continued)

Primary Examiner — Jacqueline F Stephens
(74) Attorney, Agent, or Firm — Daniel S. Albrecht

(57) ABSTRACT

An absorbent article includes a longitudinal axis extending in a longitudinal direction of the article, a liquid permeable topsheet, a liquid impermeable backsheet, and an absorbent core disposed between the topsheet and backsheet. The absorbent core includes a superabsorbent polymer. The article further includes an acquisition-distribution layer; and at least one channel positioned within a layer located between the topsheet and the backsheet, the at least one channel being substantially free of fibers and superabsorbent polymer. An indentation occurs in at least one of the topsheet and the backsheet that correspond to the at least one channels when the article is loaded with fluid.

19 Claims, 7 Drawing Sheets

Related U.S. Application Data continuation of application No. 15/959,568, filed on Apr. 23, 2018, now Pat. No. 10,966,885, which is a continuation of application No. 15/236,548, filed on Aug. 15, 2016, now abandoned, which is a continuation of application No. 15/161,331, filed on May 23, 2016, now abandoned, which is a continuation of application No. 14/540,079, filed on Nov. 13, 2014, now Pat. No. 9,375,358, which is a continuation of application No. 14/100,059, filed on Dec. 9, 2013, now Pat. No. 10,022,280.

(51) Int. Cl.
*A61F 13/49* (2006.01)
*A61F 13/532* (2006.01)
*A61F 13/534* (2006.01)
*A61F 13/539* (2006.01)
*A61F 13/53* (2006.01)
*A61F 13/531* (2006.01)
*A61F 13/537* (2006.01)

(52) U.S. Cl.
CPC .. *A61F 13/49001* (2013.01); *A61F 13/49017* (2013.01); *A61F 13/5323* (2013.01); *A61F 13/539* (2013.01); *A61F 2013/49092* (2013.01); *A61F 2013/49093* (2013.01); *A61F 2013/530226* (2013.01); *A61F 2013/530481* (2013.01); *A61F 2013/530489* (2013.01); *A61F 2013/530897* (2013.01); *A61F 2013/5315* (2013.01); *A61F 13/537* (2013.01); *A61F 2013/53765* (2013.01); *A61F 2013/53778* (2013.01)

(58) Field of Classification Search
CPC .................. A61F 13/539; A61F 13/537; A61F 2013/49092; A61F 2013/49093; A61F 2013/530226; A61F 2013/530481; A61F 2013/530489; A61F 2013/530897; A61F 2013/535; A61F 2013/53765; A61F 2013/53778
See application file for complete search history.

(56) References Cited

U.S. PATENT DOCUMENTS

| | | |
|---|---|---|
| 1,733,997 A | 10/1929 | Steven |
| 1,734,499 A | 11/1929 | Davis |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Norden |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lonberg-holm |
| 2,890,701 A | 6/1959 | Weinman |
| 2,898,912 A | 8/1959 | Adams |
| 2,931,361 A | 4/1960 | Sostrin |
| 2,977,957 A | 4/1961 | Joseph |
| 3,071,138 A | 1/1963 | Garcia |
| 3,180,335 A | 4/1965 | Duncan et al. |
| 3,207,158 A | 9/1965 | Yoshitake et al. |
| 3,227,160 A | 1/1966 | Margaret |
| 3,386,442 A | 6/1968 | Reinhardt |
| 3,411,504 A | 11/1968 | Glassman |
| 3,561,446 A | 2/1971 | Jones, Sr. |
| 3,572,342 A | 3/1971 | Lindquist |
| 3,572,432 A | 3/1971 | Aulick |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones, Sr. |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand |
| 3,828,784 A | 8/1974 | Zoephel |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | Macdonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,287,153 A | 9/1981 | Towsend |
| 4,296,750 A | 10/1981 | Woon et al. |
| 4,315,508 A | 2/1982 | Bolick et al. |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr |
| 4,469,710 A | 9/1984 | Rielley et al. |
| 4,475,912 A | 10/1984 | Coates |
| 4,490,148 A | 12/1984 | Beckestrom |
| 4,507,438 A | 3/1985 | Obayashi et al. |
| 4,515,595 A | 5/1985 | Kievit |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola |
| 4,578,072 A | 3/1986 | Lancaster |

(56) References Cited

U.S. PATENT DOCUMENTS

| | | |
|---|---|---|
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett et al. |
| 4,629,643 A | 12/1986 | Curro |
| 4,641,381 A | 2/1987 | Heran et al. |
| 4,643,727 A | 2/1987 | Rosenbaum |
| 4,646,510 A | 3/1987 | Mcintyre |
| 4,662,875 A | 5/1987 | Hirotsu |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussaint et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant |
| 4,704,115 A | 11/1987 | Buell |
| 4,704,116 A | 11/1987 | Enloe et al. |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| 4,741,941 A | 5/1988 | Englebert |
| 4,747,846 A | 5/1988 | Boland et al. |
| 4,753,648 A | 6/1988 | Jackson |
| 4,773,905 A | 9/1988 | Molee et al. |
| 4,784,892 A | 11/1988 | Storey et al. |
| 4,785,996 A | 11/1988 | Ziecker |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Froeidh |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,636,207 B1 | 11/1989 | Buell et al. |
| 4,886,697 A | 12/1989 | Perdelwitz, Jr. et al. |
| 4,888,231 A | 12/1989 | Angstadt |
| 4,892,528 A | 1/1990 | Suzuki |
| 4,892,535 A | 1/1990 | Bjoernberg et al. |
| 4,892,536 A | 1/1990 | Desmarais |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz |
| 4,936,839 A | 6/1990 | Molee et al. |
| 4,940,463 A | 7/1990 | Leathers et al. |
| 4,940,464 A | 7/1990 | Van |
| 4,946,527 A | 8/1990 | Battrell |
| 4,950,264 A | 8/1990 | Osborn, III |
| 4,960,477 A | 10/1990 | Mesek |
| 4,963,140 A | 10/1990 | Robertson |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen |
| 5,071,414 A | 12/1991 | Elliott |
| 5,072,687 A | 12/1991 | Mitchell et al. |
| 5,085,654 A | 2/1992 | Buell |
| 5,087,255 A | 2/1992 | Sims |
| 5,092,861 A | 3/1992 | Nomura |
| 5,102,597 A | 4/1992 | Berg et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron |
| 5,143,679 A | 9/1992 | Weber |
| 5,147,345 A | 9/1992 | Lavon |
| 5,149,334 A | 9/1992 | Berg et al. |
| 5,149,335 A | 9/1992 | Kellenberger |
| 5,151,091 A | 9/1992 | Glaug et al. |
| 5,151,092 A | 9/1992 | Buell |
| 5,156,793 A | 10/1992 | Buell |
| 5,167,653 A | 12/1992 | Igaue et al. |
| 5,167,897 A | 12/1992 | Weber |
| 5,175,046 A | 12/1992 | Nguyen |
| 5,180,622 A | 1/1993 | Lahrman et al. |
| 5,188,624 A | 2/1993 | Brunnenkant et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell |
| 5,235,515 A | 8/1993 | Ungpiyakul et al. |
| 5,242,436 A | 9/1993 | Weil |
| 5,246,431 A | 9/1993 | Minetola et al. |
| 5,246,432 A | 9/1993 | Suzuki et al. |
| 5,246,433 A | 9/1993 | Hasse |
| 5,248,309 A | 9/1993 | Serbiak |
| 5,260,345 A | 11/1993 | Desmarais |
| 5,269,775 A | 12/1993 | Freeland |
| 5,281,683 A | 1/1994 | Yano et al. |
| H1298 H | 4/1994 | Ahr et al. |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | Lavon et al. |
| 5,366,451 A | 11/1994 | Levesque |
| 5,366,782 A | 11/1994 | Curro et al. |
| 5,382,610 A | 1/1995 | Harada et al. |
| 5,387,207 A | 2/1995 | Dyer |
| 5,387,208 A | 2/1995 | Ashton |
| 5,387,209 A | 2/1995 | Yamamoto et al. |
| 5,389,095 A | 2/1995 | Suzuki et al. |
| 5,397,316 A | 3/1995 | Young |
| 5,397,317 A | 3/1995 | Thomas |
| 5,399,175 A | 3/1995 | Glaug et al. |
| 5,401,792 A | 3/1995 | Gaddam et al. |
| 5,409,771 A | 4/1995 | Dahmen et al. |
| H1440 H | 5/1995 | New et al. |
| 5,411,497 A | 5/1995 | Tanzer |
| 5,415,644 A | 5/1995 | Enloe |
| 5,425,725 A | 6/1995 | Tanzer |
| 5,429,630 A | 7/1995 | Beal et al. |
| 5,433,715 A | 7/1995 | Tanzer |
| 5,451,219 A | 9/1995 | Suzuki et al. |
| 5,451,442 A | 9/1995 | Pieniak et al. |
| 5,460,622 A | 10/1995 | Dragoo et al. |
| 5,460,623 A | 10/1995 | Emenaker et al. |
| 5,462,541 A | 10/1995 | Bruemmer et al. |

(56) References Cited

U.S. PATENT DOCUMENTS

| | | |
|---|---|---|
| 5,476,458 A | 12/1995 | Glaug et al. |
| 5,486,166 A | 1/1996 | Bishop et al. |
| 5,486,167 A | 1/1996 | Dragoo et al. |
| 5,487,736 A | 1/1996 | Van |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell |
| 5,507,736 A | 4/1996 | Clear |
| 5,507,895 A | 4/1996 | Suekane |
| 5,509,915 A | 4/1996 | Hanson |
| 5,514,104 A | 5/1996 | Cole et al. |
| 5,518,801 A | 5/1996 | Chappell |
| 5,520,674 A | 5/1996 | Lavon et al. |
| 5,522,810 A | 6/1996 | Allen, Jr. et al. |
| 5,527,300 A | 6/1996 | Sauer |
| 5,531,730 A | 7/1996 | Dreier |
| 5,532,323 A | 7/1996 | Yano et al. |
| 5,533,991 A * | 7/1996 | Kirby .................... A61F 13/512 604/383 |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe |
| 5,559,335 A | 9/1996 | Zeng et al. |
| 5,560,878 A | 10/1996 | Dragoo et al. |
| 5,562,634 A | 10/1996 | Flumene et al. |
| 5,562,646 A | 10/1996 | Goldman |
| 5,562,650 A | 10/1996 | Everett et al. |
| 5,569,234 A | 10/1996 | Buell |
| 5,571,096 A | 11/1996 | Dobrin |
| 5,574,121 A | 11/1996 | Irie et al. |
| 5,575,783 A | 11/1996 | Clear |
| 5,580,411 A | 12/1996 | Nease |
| 5,584,829 A | 12/1996 | Lavash et al. |
| 5,586,979 A | 12/1996 | Thomas |
| 5,591,152 A | 1/1997 | Buell |
| 5,591,155 A | 1/1997 | Nishikawa |
| 5,593,399 A | 1/1997 | Tanzer |
| 5,599,335 A | 2/1997 | Goldman |
| 5,601,542 A | 2/1997 | Melius |
| 5,607,414 A | 3/1997 | Richards |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | Dipalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur et al. |
| 5,624,424 A | 4/1997 | Saisaka et al. |
| 5,625,222 A | 4/1997 | Yoneda |
| 5,626,571 A | 5/1997 | Young et al. |
| 5,628,736 A | 5/1997 | Thompson |
| 5,628,741 A | 5/1997 | Buell et al. |
| 5,628,845 A | 5/1997 | Murray et al. |
| 5,635,191 A | 6/1997 | Roe |
| 5,635,271 A | 6/1997 | Zafiroglu |
| 5,637,106 A | 6/1997 | Mitchell et al. |
| 5,643,238 A | 7/1997 | Baker |
| 5,643,243 A | 7/1997 | Klemp |
| 5,643,588 A | 7/1997 | Roe |
| 5,649,914 A | 7/1997 | Glaug et al. |
| 5,650,214 A | 7/1997 | Anderson et al. |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman |
| 5,674,215 A | 10/1997 | Roennberg |
| 5,681,300 A | 10/1997 | Ahr |
| 5,683,374 A | 11/1997 | Yamamoto et al. |
| 5,685,874 A | 11/1997 | Buell et al. |
| 5,690,624 A | 11/1997 | Sasaki et al. |
| 5,690,627 A | 11/1997 | Clear et al. |
| 5,691,035 A | 11/1997 | Chappell et al. |
| 5,691,036 A | 11/1997 | Lin et al. |
| 5,695,488 A | 12/1997 | Sosalla |
| 5,700,254 A | 12/1997 | Mcdowall |
| 5,702,376 A | 12/1997 | Glaug et al. |
| 5,713,881 A | 2/1998 | Rezai et al. |
| 5,714,156 A | 2/1998 | Schmidt et al. |
| 5,147,343 B1 | 3/1998 | Kellenberger et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall |
| H1732 H | 6/1998 | Jhonson |
| 5,762,641 A | 6/1998 | Bewick-sonntag |
| 5,766,388 A | 6/1998 | Pelley et al. |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani et al. |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka et al. |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,853,402 A | 12/1998 | Faulks et al. |
| 5,855,572 A | 1/1999 | Schmidt |
| 5,858,013 A | 1/1999 | Kling |
| 5,858,515 A | 1/1999 | Stokes et al. |
| 5,865,823 A | 2/1999 | Curro |
| 5,865,824 A | 2/1999 | Chen et al. |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima et al. |
| 5,891,544 A | 4/1999 | Chappell et al. |
| 5,897,545 A | 4/1999 | Kline |
| 5,904,673 A | 5/1999 | Roe et al. |
| 5,925,439 A | 7/1999 | Haubach |
| 5,928,184 A | 7/1999 | Etheredge et al. |
| 5,931,825 A | 8/1999 | Kuen et al. |
| 5,938,648 A | 8/1999 | Beck |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline |
| 5,964,743 A | 10/1999 | Abuto et al. |
| 5,968,025 A | 10/1999 | Roe |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles |
| 6,010,490 A | 1/2000 | Freeland et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |

(56) References Cited

U.S. PATENT DOCUMENTS

| | | |
|---|---|---|
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski et al. |
| 6,080,909 A | 6/2000 | Oesterdahl et al. |
| 6,083,210 A | 7/2000 | Young et al. |
| 6,090,994 A | 7/2000 | Chen |
| 6,091,336 A | 7/2000 | Zand et al. |
| 6,093,474 A | 7/2000 | Sironi |
| 6,099,515 A | 8/2000 | Sugito |
| 6,102,892 A | 8/2000 | Putzer et al. |
| 6,103,814 A | 8/2000 | Vandrongelen et al. |
| 6,107,537 A | 8/2000 | Elder |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak et al. |
| 6,143,821 A | 11/2000 | Houben |
| 6,152,908 A | 11/2000 | Widlund et al. |
| 6,156,023 A | 12/2000 | Yoshioka |
| 6,156,424 A | 12/2000 | Taylor |
| 6,160,197 A | 12/2000 | Lassen et al. |
| 6,165,160 A | 12/2000 | Suzuki |
| 6,174,302 B1 | 1/2001 | Kumasaka |
| 6,177,606 B1 | 1/2001 | Etheredge et al. |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,221,460 B1 | 4/2001 | Weber et al. |
| 6,231,556 B1 | 5/2001 | Osborn, III |
| 6,231,566 B1 | 5/2001 | Lai |
| 6,238,380 B1 | 5/2001 | Sasaki |
| 6,241,714 B1 | 6/2001 | Raidel et al. |
| 6,241,716 B1 | 6/2001 | Roennberg |
| 6,254,294 B1 | 7/2001 | Muhar |
| 6,258,996 B1 | 7/2001 | Goldman |
| 6,261,679 B1 | 7/2001 | Chen et al. |
| 6,264,639 B1 | 7/2001 | Sauer |
| 6,265,488 B1 | 7/2001 | Nagasuna et al. |
| 6,290,686 B1 | 9/2001 | Tanzer |
| 6,306,122 B1 | 10/2001 | Narawa et al. |
| 6,307,119 B1 | 10/2001 | Cammarota |
| 6,315,765 B1 | 11/2001 | Datta et al. |
| 6,319,239 B1 | 11/2001 | Daniels |
| 6,322,552 B1 | 11/2001 | Blenke et al. |
| 6,325,787 B1 | 12/2001 | Roe et al. |
| 6,326,525 B1 | 12/2001 | Hamajima et al. |
| 6,330,735 B1 | 12/2001 | Hahn et al. |
| 6,334,858 B1 | 1/2002 | Ronnberg et al. |
| 6,336,922 B1 | 1/2002 | Vangompel et al. |
| 6,340,611 B1 | 1/2002 | Shimizu et al. |
| 6,342,715 B1 | 1/2002 | Shimizu et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin |
| 6,383,960 B1 | 5/2002 | Everett et al. |
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | Mcfall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,420,622 B1 | 7/2002 | Johnston et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline |
| 6,432,099 B2 | 8/2002 | Roennberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Cleveland |
| 6,461,342 B2 | 10/2002 | Tanji et al. |
| 6,461,343 B1 | 10/2002 | Schaefer et al. |
| 6,472,478 B1 | 10/2002 | Funk |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler et al. |
| 6,506,961 B1 | 1/2003 | Levy |
| 6,515,195 B1 | 2/2003 | Lariviere et al. |
| 6,517,525 B1 | 2/2003 | Berthou et al. |
| 6,518,479 B1 | 2/2003 | Graef et al. |
| 6,520,947 B1 | 2/2003 | Tilly et al. |
| 6,521,811 B1 | 2/2003 | Lassen et al. |
| 6,521,812 B1 | 2/2003 | Graef et al. |
| 6,524,294 B1 | 2/2003 | Hilston et al. |
| 6,525,240 B1 | 2/2003 | Graef et al. |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer et al. |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld et al. |
| 6,585,713 B1 | 7/2003 | Lemahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,613,955 B1 | 9/2003 | Lindsay et al. |
| 6,630,054 B1 | 10/2003 | Graef et al. |
| 6,632,209 B1 | 10/2003 | Chmielewski |
| 6,632,504 B1 | 10/2003 | Gillespie |
| 6,645,569 B2 | 11/2003 | Cramer |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya et al. |
| 6,667,424 B1 | 12/2003 | Hamilton |
| 6,670,522 B1 | 12/2003 | Graef et al. |
| 6,673,982 B1 | 1/2004 | Chen |
| 6,673,983 B1 | 1/2004 | Graef et al. |

(56) References Cited

U.S. PATENT DOCUMENTS

| | | |
|---|---|---|
| 6,673,985 B2 | 1/2004 | Mizutani et al. |
| 6,682,515 B1 | 1/2004 | Mizutani et al. |
| 6,682,516 B2 | 1/2004 | Johnston et al. |
| 6,689,115 B1 | 2/2004 | Coenen et al. |
| 6,689,934 B2 | 2/2004 | Dodge et al. |
| 6,695,827 B2 | 2/2004 | Chen |
| 6,700,034 B1 | 3/2004 | Lindsay et al. |
| 6,700,036 B2 | 3/2004 | Thomas et al. |
| 6,703,538 B2 | 3/2004 | Lassen et al. |
| 6,705,465 B2 | 3/2004 | Ling et al. |
| 6,706,129 B2 | 3/2004 | Ando et al. |
| 6,706,943 B2 | 3/2004 | Onishi et al. |
| 6,710,224 B2 | 3/2004 | Chmielewski et al. |
| 6,710,225 B1 | 3/2004 | Everett et al. |
| 6,716,205 B2 | 4/2004 | Coenen et al. |
| 6,716,441 B1 | 4/2004 | Osborne et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef et al. |
| 6,746,976 B1 | 6/2004 | Urankar et al. |
| 6,790,798 B1 | 9/2004 | Suzuki |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Coenen et al. |
| 6,858,771 B2 | 2/2005 | Yoshimasa et al. |
| 6,863,933 B2 | 3/2005 | Cramer |
| 6,863,960 B2 | 3/2005 | Curro et al. |
| 6,867,345 B2 | 3/2005 | Shimoe et al. |
| 6,867,346 B1 | 3/2005 | Dopps et al. |
| 6,878,433 B2 | 4/2005 | Curro |
| 6,878,647 B1 | 4/2005 | Rezai |
| 6,880,211 B2 | 4/2005 | Jackson et al. |
| 6,891,080 B2 | 5/2005 | Minato et al. |
| 6,903,243 B1 | 6/2005 | Burton |
| 6,904,865 B2 | 6/2005 | Klofta et al. |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito et al. |
| 6,929,629 B2 | 8/2005 | Drevik et al. |
| 6,939,914 B2 | 9/2005 | Qin et al. |
| 6,946,585 B2 | 9/2005 | London |
| 6,953,451 B2 | 10/2005 | Berba et al. |
| 6,955,667 B1 | 10/2005 | Tanaka et al. |
| 6,955,733 B2 | 10/2005 | Miller |
| 6,962,578 B1 | 11/2005 | Lavon |
| 6,962,645 B2 | 11/2005 | Graef et al. |
| 6,965,058 B1 | 11/2005 | Raidel |
| 6,969,781 B2 | 11/2005 | Graef et al. |
| 6,972,010 B2 | 12/2005 | Pesce et al. |
| 6,972,011 B2 | 12/2005 | Mori |
| 6,974,892 B2 | 12/2005 | Decarvalho et al. |
| 6,979,564 B2 | 12/2005 | Glucksmann et al. |
| 6,982,052 B2 | 1/2006 | Daniels et al. |
| 7,001,167 B2 | 2/2006 | Venturino et al. |
| 7,014,632 B2 | 3/2006 | Takino et al. |
| 7,015,370 B2 | 3/2006 | Watanabe et al. |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita et al. |
| 7,067,711 B2 | 6/2006 | Kuroda et al. |
| 7,073,373 B2 | 7/2006 | La |
| 7,078,583 B2 | 7/2006 | Kudo et al. |
| 7,090,665 B2 | 8/2006 | Ohashi et al. |
| 7,108,759 B2 | 9/2006 | You et al. |
| 7,108,916 B2 | 9/2006 | Ehrnsperger |
| 7,112,621 B2 | 9/2006 | Rohrbaugh |
| 7,122,713 B2 | 10/2006 | Komatsu et al. |
| 7,125,470 B2 | 10/2006 | Graef et al. |
| 7,132,585 B2 | 11/2006 | Kudo et al. |
| 7,147,628 B2 | 12/2006 | Drevik |
| 7,150,729 B2 | 12/2006 | Shimada et al. |
| 7,154,019 B2 | 12/2006 | Mishima et al. |
| 7,160,281 B2 | 1/2007 | Leminh et al. |
| 7,163,528 B2 | 1/2007 | Christon |
| 7,166,190 B2 | 1/2007 | Graef et al. |
| 7,169,136 B2 | 1/2007 | Otsubo et al. |
| 7,183,360 B2 | 2/2007 | Daniel et al. |
| 7,189,888 B2 | 3/2007 | Wang et al. |
| 7,196,241 B2 | 3/2007 | Kinoshita et al. |
| 7,199,211 B2 | 4/2007 | Popp et al. |
| 7,204,830 B2 | 4/2007 | Mishima et al. |
| 7,207,978 B2 | 4/2007 | Takino et al. |
| 7,219,403 B2 | 5/2007 | Miyamoto et al. |
| 7,220,251 B2 | 5/2007 | Otsubo et al. |
| 7,241,280 B2 | 7/2007 | Christon et al. |
| 7,250,481 B2 | 7/2007 | Jaworek et al. |
| 7,252,657 B2 | 8/2007 | Mishima et al. |
| 7,265,258 B2 | 9/2007 | Hamilton |
| 7,270,651 B2 | 9/2007 | Adams |
| 7,285,178 B2 | 10/2007 | Mischler |
| 7,306,582 B2 | 12/2007 | Adams |
| 7,311,696 B2 | 12/2007 | Christon et al. |
| 7,311,968 B2 | 12/2007 | Ehrnsperger et al. |
| 7,312,372 B2 | 12/2007 | Miyama et al. |
| 7,318,820 B2 | 1/2008 | Lavon et al. |
| 7,329,244 B2 | 2/2008 | Otsubo et al. |
| 7,329,246 B2 | 2/2008 | Kinoshita et al. |
| 7,335,810 B2 | 2/2008 | Yoshimasa et al. |
| 7,377,914 B2 | 5/2008 | Lavon |
| 7,429,689 B2 | 9/2008 | Chen |
| 7,435,244 B2 | 10/2008 | Schroer, Jr. et al. |
| 7,465,373 B2 | 12/2008 | Graef et al. |
| 7,500,969 B2 | 3/2009 | Mishima et al. |
| 7,504,552 B2 | 3/2009 | Tamura et al. |
| 7,504,553 B2 | 3/2009 | Nagahara et al. |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi et al. |
| 7,550,646 B2 | 6/2009 | Tamura et al. |
| 7,563,257 B2 | 7/2009 | Nakajima et al. |
| 7,588,561 B2 | 9/2009 | Kenmochi et al. |
| 7,594,904 B2 | 9/2009 | Rosenfeld et al. |
| 7,598,428 B2 | 10/2009 | Gustavsson et al. |
| 7,625,363 B2 | 12/2009 | Yoshimasa et al. |
| 7,641,642 B2 | 1/2010 | Murai et al. |
| 7,648,490 B2 | 1/2010 | Kuroda et al. |
| 7,652,111 B2 | 1/2010 | Hermeling et al. |
| 7,666,173 B2 | 2/2010 | Mishima et al. |
| 7,666,174 B2 | 2/2010 | Onishi et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld et al. |
| 7,696,402 B2 | 4/2010 | Nishikawa et al. |
| 7,708,725 B2 | 5/2010 | Tamagawa et al. |
| 7,717,150 B2 | 5/2010 | Manabe et al. |
| 7,718,249 B2 | 5/2010 | Russell et al. |
| 7,718,844 B2 | 5/2010 | Olson |
| 7,722,587 B2 | 5/2010 | Suzuki et al. |
| 7,722,590 B2 | 5/2010 | Tsuji et al. |
| 7,727,217 B2 | 6/2010 | Hancock-cooke |
| 7,736,351 B2 | 6/2010 | Nigam et al. |
| 7,737,324 B2 | 6/2010 | Lavon et al. |
| 7,744,576 B2 | 6/2010 | Busam |
| 7,744,578 B2 | 6/2010 | Tanio et al. |
| 7,750,203 B2 | 7/2010 | Becker et al. |
| 7,754,822 B2 | 7/2010 | Daniel et al. |
| 7,754,940 B2 | 7/2010 | Brisebois et al. |
| 7,759,540 B2 | 7/2010 | Litvay et al. |
| 7,763,004 B2 | 7/2010 | Lavon |
| 7,767,875 B2 | 8/2010 | Olson et al. |
| 7,767,876 B2 | 8/2010 | Davis et al. |
| 7,767,878 B2 | 8/2010 | Suzuki |
| 7,772,420 B2 | 8/2010 | Hermeling et al. |

(56) References Cited

U.S. PATENT DOCUMENTS

| | | |
|---|---|---|
| 7,786,341 B2 | 8/2010 | Schneider et al. |
| 7,795,492 B2 | 9/2010 | Vartiainen |
| 7,803,145 B2 | 9/2010 | Rosenfeld et al. |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao et al. |
| 7,857,797 B2 | 12/2010 | Kudo et al. |
| 7,858,842 B2 | 12/2010 | Komatsu et al. |
| 7,884,259 B2 | 2/2011 | Hanao et al. |
| 7,888,549 B2 | 2/2011 | Jansson et al. |
| 7,910,797 B2 | 3/2011 | Nandrea et al. |
| 7,931,636 B2 | 4/2011 | Lavon et al. |
| 7,935,207 B2 | 5/2011 | Zhao et al. |
| 7,935,861 B2 | 5/2011 | Suzuki |
| 7,938,813 B2 | 5/2011 | Wang et al. |
| 7,942,858 B2 | 5/2011 | Francoeur et al. |
| 7,951,126 B2 | 5/2011 | Nanjyo et al. |
| 7,956,236 B2 | 6/2011 | Ponomarenko et al. |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima et al. |
| 8,030,536 B2 | 10/2011 | Ponomarenko et al. |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe et al. |
| 8,124,828 B2 | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda et al. |
| 8,178,747 B2 | 5/2012 | Venturino et al. |
| 8,183,430 B2 | 5/2012 | Haakansson et al. |
| 8,186,296 B2 | 5/2012 | Brown |
| 8,187,239 B2 | 5/2012 | Lavon |
| 8,187,240 B2 | 5/2012 | Busam et al. |
| 8,198,506 B2 | 6/2012 | Venturino et al. |
| 8,211,815 B2 | 7/2012 | Baker et al. |
| 8,236,715 B2 | 8/2012 | Schmidt et al. |
| 8,237,012 B2 | 8/2012 | Miyama et al. |
| 8,246,594 B2 | 8/2012 | Sperl et al. |
| 8,258,367 B2 | 9/2012 | Lawson et al. |
| 8,268,424 B1 | 9/2012 | Suzuki et al. |
| 8,273,943 B2 | 9/2012 | Noda et al. |
| 8,282,617 B2 | 10/2012 | Kaneda |
| 8,283,516 B2 | 10/2012 | Litvay |
| 8,317,766 B2 | 11/2012 | Naoto et al. |
| 8,317,768 B2 | 11/2012 | Larsson |
| 8,319,005 B2 | 11/2012 | Becker et al. |
| 8,343,123 B2 | 1/2013 | Noda et al. |
| 8,343,296 B2 | 1/2013 | Blessing et al. |
| 8,343,447 B2 | 1/2013 | Shibayama et al. |
| 8,360,977 B2 | 1/2013 | Marttila et al. |
| 8,361,047 B2 | 1/2013 | Mukai et al. |
| 8,377,025 B2 | 2/2013 | Nakajima et al. |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,380 B2 | 10/2013 | Brownlee |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | Lavon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |
| 9,056,034 B2 | 6/2015 | Akiyama |
| 9,066,831 B2 | 6/2015 | Moriya et al. |
| 9,326,896 B2 | 5/2016 | Schäfer et al. |
| 9,375,358 B2 | 6/2016 | Ehrnsperger et al. |
| 10,022,280 B2 | 7/2018 | Ehrnsperger et al. |
| 10,966,885 B2 | 4/2021 | Ehrnsperger |
| 2001/0007065 A1 | 7/2001 | Blanchard et al. |
| 2001/0008964 A1 | 7/2001 | Kurata et al. |
| 2001/0016548 A1 | 8/2001 | Kugler et al. |
| 2001/0020157 A1 | 9/2001 | Mizutani et al. |
| 2001/0037101 A1 | 11/2001 | Allan et al. |
| 2001/0044610 A1 | 11/2001 | Kim et al. |
| 2002/0007167 A1 | 1/2002 | Dan et al. |
| 2002/0007169 A1 | 1/2002 | Graef |
| 2002/0016122 A1 | 2/2002 | Curro |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi et al. |
| 2002/0072471 A1 | 6/2002 | Ikeuchi et al. |
| 2002/0082575 A1 | 6/2002 | Dan et al. |
| 2002/0087139 A1 | 7/2002 | Coenen et al. |
| 2002/0095126 A1 | 7/2002 | Inoue et al. |
| 2002/0095127 A1 | 7/2002 | Fish et al. |
| 2002/0102392 A1 | 8/2002 | Fish et al. |
| 2002/0115969 A1 | 8/2002 | Mori et al. |
| 2002/0115972 A1 | 8/2002 | Dabi et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Coenen |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl |
| 2003/0109839 A1 | 6/2003 | Costea |
| 2003/0114811 A1 | 6/2003 | Christon et al. |
| 2003/0114816 A1 | 6/2003 | Underhill et al. |
| 2003/0114818 A1 | 6/2003 | Benecke |
| 2003/0115969 A1 | 6/2003 | Koyano |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135181 A1 | 7/2003 | Chen |
| 2003/0135182 A1 | 7/2003 | Woon |
| 2003/0139712 A1 | 7/2003 | Dodge et al. |
| 2003/0139715 A1 | 7/2003 | Dodge et al. |
| 2003/0139718 A1 | 7/2003 | Graef et al. |
| 2003/0144642 A1 | 7/2003 | Dopps et al. |
| 2003/0144644 A1 | 7/2003 | Murai |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee |
| 2003/0167045 A1 | 9/2003 | Graef et al. |
| 2003/0171727 A1 | 9/2003 | Graef et al. |
| 2003/0208175 A1 | 11/2003 | Gross et al. |
| 2003/0225385 A1 | 12/2003 | Glaug et al. |
| 2003/0233082 A1 | 12/2003 | Kline |
| 2003/0236510 A1 | 12/2003 | Yasumura et al. |
| 2003/0236512 A1 | 12/2003 | Baker |
| 2004/0019338 A1 | 1/2004 | Litvay et al. |
| 2004/0022998 A1 | 2/2004 | Miyamoto et al. |

(56) References Cited

U.S. PATENT DOCUMENTS

| | | |
|---|---|---|
| 2004/0033750 A1 | 2/2004 | Everett et al. |
| 2004/0063367 A1 | 4/2004 | Dodge et al. |
| 2004/0064113 A1 | 4/2004 | Erdman |
| 2004/0064115 A1 | 4/2004 | Arora et al. |
| 2004/0064116 A1 | 4/2004 | Arora et al. |
| 2004/0064125 A1 | 4/2004 | Justmann et al. |
| 2004/0065420 A1 | 4/2004 | Graef et al. |
| 2004/0082928 A1 | 4/2004 | Pesce et al. |
| 2004/0097895 A1 | 5/2004 | Busam |
| 2004/0122411 A1 | 6/2004 | Hancock-cooke |
| 2004/0127131 A1 | 7/2004 | Potnis |
| 2004/0127871 A1 | 7/2004 | Odorzynski et al. |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko |
| 2004/0162536 A1 | 8/2004 | Becker |
| 2004/0167486 A1 | 8/2004 | Busam |
| 2004/0167489 A1 | 8/2004 | Kellenberger et al. |
| 2004/0170813 A1 | 9/2004 | Digiacomantonio |
| 2004/0193127 A1 | 9/2004 | Hansson et al. |
| 2004/0214499 A1 | 10/2004 | Qin et al. |
| 2004/0215160 A1 | 10/2004 | Chmielewski et al. |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio |
| 2004/0260259 A1 | 12/2004 | Baker |
| 2005/0001929 A1 | 1/2005 | Ochial et al. |
| 2005/0004543 A1 | 1/2005 | Schroer et al. |
| 2005/0004548 A1 | 1/2005 | Otsubo et al. |
| 2005/0008839 A1 | 1/2005 | Cramer |
| 2005/0018258 A1 | 1/2005 | Miyagi et al. |
| 2005/0027267 A1 | 2/2005 | Van et al. |
| 2005/0038401 A1 | 2/2005 | Suzuki et al. |
| 2005/0070867 A1 | 3/2005 | Beruda et al. |
| 2005/0085784 A1 | 4/2005 | Leminh et al. |
| 2005/0090789 A1 | 4/2005 | Graef et al. |
| 2005/0137543 A1 | 6/2005 | Underhill et al. |
| 2005/0148258 A1 | 7/2005 | Chakravarty et al. |
| 2005/0148961 A1 | 7/2005 | Sosalla |
| 2005/0148990 A1 | 7/2005 | Shimoe et al. |
| 2005/0154363 A1 | 7/2005 | Minato et al. |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | Lavon et al. |
| 2005/0215752 A1 | 9/2005 | Popp et al. |
| 2005/0217791 A1 | 10/2005 | Costello |
| 2005/0229543 A1 | 10/2005 | Tippey |
| 2005/0234414 A1 | 10/2005 | Liu |
| 2005/0245684 A1 | 11/2005 | Daniel et al. |
| 2005/0288645 A1 | 12/2005 | Lavon |
| 2005/0288646 A1 | 12/2005 | Lavon |
| 2006/0004334 A1 | 1/2006 | Schlinz et al. |
| 2006/0021695 A1 | 2/2006 | Blessing |
| 2006/0024433 A1 | 2/2006 | Blessing |
| 2006/0027101 A1 | 2/2006 | Pan et al. |
| 2006/0069367 A1 | 3/2006 | Widlund et al. |
| 2006/0069371 A1 | 3/2006 | Ohashi |
| 2006/0073969 A1 | 4/2006 | Torii et al. |
| 2006/0081348 A1 | 4/2006 | Graef et al. |
| 2006/0129114 A1 | 6/2006 | Mason et al. |
| 2006/0142724 A1 | 6/2006 | Watanabe et al. |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt |
| 2006/0178071 A1 | 8/2006 | Schmidt et al. |
| 2006/0184146 A1* | 8/2006 | Suzuki .................. A61F 13/535 604/358 |
| 2006/0184149 A1 | 8/2006 | Kasai et al. |
| 2006/0189954 A1 | 8/2006 | Kudo |
| 2006/0202380 A1 | 9/2006 | Bentley et al. |
| 2006/0206091 A1 | 9/2006 | Cole et al. |
| 2006/0211828 A1 | 9/2006 | Daniel et al. |
| 2006/0240229 A1 | 10/2006 | Ehrnsperger et al. |
| 2006/0264860 A1 | 11/2006 | Lavon |
| 2006/0264861 A1 | 11/2006 | Lavon et al. |
| 2006/0271010 A1 | 11/2006 | Lavon |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof |
| 2007/0044903 A1 | 3/2007 | Wisneski et al. |
| 2007/0049892 A1 | 3/2007 | Lord et al. |
| 2007/0049897 A1 | 3/2007 | Lavon et al. |
| 2007/0073253 A1 | 3/2007 | Miyama et al. |
| 2007/0078422 A1 | 4/2007 | Glaug et al. |
| 2007/0083175 A1 | 4/2007 | Van et al. |
| 2007/0088308 A1 | 4/2007 | Ehrnsperger et al. |
| 2007/0093164 A1* | 4/2007 | Nakaoka .................. A61F 13/536 442/385 |
| 2007/0093767 A1 | 4/2007 | Carlucci et al. |
| 2007/0100307 A1 | 5/2007 | Nomoto et al. |
| 2007/0106013 A1 | 5/2007 | Adachi et al. |
| 2007/0118087 A1 | 5/2007 | Flohr |
| 2007/0123834 A1 | 5/2007 | Mcdowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug et al. |
| 2007/0219521 A1 | 9/2007 | Hird |
| 2007/0219523 A1 | 9/2007 | Bruun et al. |
| 2007/0239125 A9 | 10/2007 | Erdman et al. |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda et al. |
| 2007/0282290 A1 | 12/2007 | Cole et al. |
| 2007/0282291 A1 | 12/2007 | Cole et al. |
| 2007/0287971 A1 | 12/2007 | Roe et al. |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda et al. |
| 2008/0125735 A1 | 5/2008 | Busam |
| 2008/0132864 A1 | 6/2008 | Lawson et al. |
| 2008/0208154 A1 | 8/2008 | Oetjen |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto et al. |
| 2008/0268194 A1 | 10/2008 | Kim et al. |
| 2008/0274227 A1 | 11/2008 | Boatman et al. |
| 2008/0281287 A1 | 11/2008 | Marcelo et al. |
| 2008/0294140 A1 | 11/2008 | Ecker et al. |
| 2008/0312617 A1 | 12/2008 | Hundorf |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf |
| 2008/0312623 A1 | 12/2008 | Hundorf et al. |
| 2008/0312624 A1 | 12/2008 | Hundorf |
| 2008/0312625 A1 | 12/2008 | Hundorf et al. |
| 2008/0312627 A1 | 12/2008 | Takeuchi et al. |
| 2008/0312628 A1 | 12/2008 | Hundorf et al. |
| 2009/0056867 A1 | 3/2009 | Moriura et al. |
| 2009/0058994 A1 | 3/2009 | Kao et al. |
| 2009/0062760 A1 | 3/2009 | Wright et al. |
| 2009/0112173 A1 | 4/2009 | Bissah et al. |
| 2009/0112175 A1 | 4/2009 | Bissah et al. |
| 2009/0157022 A1 | 6/2009 | Macdonald et al. |
| 2009/0192035 A1 | 7/2009 | Stueven et al. |
| 2009/0240220 A1 | 9/2009 | Macdonald et al. |
| 2009/0247977 A1 | 10/2009 | Takeuchi |
| 2009/0258994 A1 | 10/2009 | Stueven et al. |

(56) References Cited

U.S. PATENT DOCUMENTS

| | | |
|---|---|---|
| 2009/0270825 A1 | 10/2009 | Wciorka et al. |
| 2009/0298963 A1 | 12/2009 | Matsumoto et al. |
| 2009/0299312 A1 | 12/2009 | Macdonald et al. |
| 2009/0306618 A1 | 12/2009 | Kudo et al. |
| 2009/0318884 A1 | 12/2009 | Meyer et al. |
| 2009/0326494 A1 | 12/2009 | Uchida et al. |
| 2009/0326497 A1 | 12/2009 | Schmidt |
| 2010/0051166 A1* | 3/2010 | Hundorf ............... B05C 19/00 156/387 |
| 2010/0062165 A1 | 3/2010 | Suzuki et al. |
| 2010/0062934 A1 | 3/2010 | Suzuki et al. |
| 2010/0063470 A1 | 3/2010 | Suzuki et al. |
| 2010/0065986 A1 | 3/2010 | Nakamura et al. |
| 2010/0068520 A1 | 3/2010 | Stueven |
| 2010/0100065 A1 | 4/2010 | De et al. |
| 2010/0115237 A1 | 5/2010 | Brewer et al. |
| 2010/0121296 A1 | 5/2010 | Noda et al. |
| 2010/0137773 A1 | 6/2010 | Gross et al. |
| 2010/0137823 A1 | 6/2010 | Corneliusson et al. |
| 2010/0198179 A1 | 8/2010 | Noda et al. |
| 2010/0228210 A1 | 9/2010 | Busam |
| 2010/0241096 A1 | 9/2010 | Lavon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii et al. |
| 2010/0274210 A1 | 10/2010 | Noda et al. |
| 2010/0305537 A1 | 12/2010 | Ashton |
| 2010/0312208 A1 | 12/2010 | Bond et al. |
| 2010/0324521 A1 | 12/2010 | Mukai et al. |
| 2010/0324523 A1 | 12/2010 | Mukai et al. |
| 2011/0034603 A1 | 2/2011 | Fujino et al. |
| 2011/0041999 A1 | 2/2011 | Hundorf et al. |
| 2011/0046592 A1 | 2/2011 | Nishikawa et al. |
| 2011/0060301 A1 | 3/2011 | Nishikawa et al. |
| 2011/0060303 A1 | 3/2011 | Bissah et al. |
| 2011/0066127 A1 | 3/2011 | Kuwano et al. |
| 2011/0071486 A1 | 3/2011 | Harada et al. |
| 2011/0092944 A1 | 4/2011 | Sagisaka et al. |
| 2011/0112498 A1 | 5/2011 | Nhan et al. |
| 2011/0125120 A1 | 5/2011 | Nishitani et al. |
| 2011/0130732 A1 | 6/2011 | Jackels et al. |
| 2011/0130737 A1 | 6/2011 | Sagisaka et al. |
| 2011/0137276 A1 | 6/2011 | Yoshikawa |
| 2011/0144602 A1 | 6/2011 | Long |
| 2011/0144604 A1 | 6/2011 | Noda et al. |
| 2011/0144606 A1 | 6/2011 | Nandrea et al. |
| 2011/0152813 A1 | 6/2011 | Ellingson |
| 2011/0166540 A1 | 7/2011 | Yang |
| 2011/0172630 A1 | 7/2011 | Nomoto et al. |
| 2011/0174430 A1 | 7/2011 | Zhao et al. |
| 2011/0196330 A1 | 8/2011 | Hammons |
| 2011/0208147 A1 | 8/2011 | Kawakami et al. |
| 2011/0250413 A1 | 10/2011 | Lu |
| 2011/0268932 A1 | 11/2011 | Catalan |
| 2011/0274834 A1 | 11/2011 | Brown et al. |
| 2011/0288513 A1 | 11/2011 | Hundorf et al. |
| 2011/0288514 A1 | 11/2011 | Kuroda et al. |
| 2011/0295222 A1 | 12/2011 | Becker et al. |
| 2011/0319846 A1 | 12/2011 | Rinnert et al. |
| 2011/0319848 A1 | 12/2011 | Mckiernan |
| 2011/0319851 A1 | 12/2011 | Kudo et al. |
| 2012/0004633 A1 | 1/2012 | R. Marcelo |
| 2012/0016326 A1 | 1/2012 | Brennan et al. |
| 2012/0022479 A1 | 1/2012 | Cotton |
| 2012/0035566 A1 | 2/2012 | Sagisaka et al. |
| 2012/0035576 A1 | 2/2012 | Ichikawa et al. |
| 2012/0041405 A1 | 2/2012 | Alkmin et al. |
| 2012/0064792 A1 | 3/2012 | Bauduin |
| 2012/0071848 A1 | 3/2012 | Zhang et al. |
| 2012/0165771 A1 | 6/2012 | Ruman et al. |
| 2012/0165776 A1 | 6/2012 | Mcgregor |
| 2012/0170779 A1 | 7/2012 | Hildebrandt |
| 2012/0175056 A1 | 7/2012 | Tsang et al. |
| 2012/0184934 A1 | 7/2012 | Venturino et al. |
| 2012/0220972 A1 | 8/2012 | Kawamura et al. |
| 2012/0226253 A1 | 9/2012 | Urushihara |
| 2012/0232514 A1 | 9/2012 | Baker et al. |
| 2012/0238977 A1 | 9/2012 | Oku et al. |
| 2012/0253306 A1 | 10/2012 | Otsubo et al. |
| 2012/0256750 A1 | 10/2012 | Novak |
| 2012/0271262 A1 | 10/2012 | Venturino et al. |
| 2012/0312491 A1 | 12/2012 | Jackels |
| 2012/0316046 A1 | 12/2012 | Jackels et al. |
| 2012/0316523 A1 | 12/2012 | Hippe |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0316530 A1 | 12/2012 | Armstrong-ostle et al. |
| 2012/0323195 A1 | 12/2012 | Ehrnsperger et al. |
| 2012/0323201 A1 | 12/2012 | Bissah et al. |
| 2012/0323202 A1 | 12/2012 | Bissah et al. |
| 2013/0012093 A1 | 1/2013 | Bond et al. |
| 2013/0035656 A1 | 2/2013 | Moriya et al. |
| 2013/0041334 A1 | 2/2013 | Prioleau et al. |
| 2013/0066290 A1 | 3/2013 | Kawakami et al. |
| 2013/0178811 A1 | 7/2013 | Kikuchi et al. |
| 2013/0211354 A1 | 8/2013 | Tsuji et al. |
| 2013/0211358 A1 | 8/2013 | Kikkawa et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van |
| 2013/0240125 A1 | 9/2013 | Heinz et al. |
| 2013/0310784 A1 | 11/2013 | Bryant |
| 2013/0331806 A1 | 12/2013 | Rosati et al. |
| 2014/0005622 A1 | 1/2014 | Wirtz |
| 2014/0005623 A1 | 1/2014 | Wirtz et al. |
| 2014/0005625 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0102183 A1 | 4/2014 | Agami et al. |
| 2014/0121623 A1 | 5/2014 | Kirby et al. |
| 2014/0121625 A1 | 5/2014 | Kirby et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163502 A1 | 6/2014 | Arizti |
| 2014/0163503 A1 | 6/2014 | Arizti |
| 2014/0163506 A1 | 6/2014 | Roe |
| 2014/0163511 A1 | 6/2014 | Roe et al. |
| 2014/0171893 A1 | 6/2014 | Lawson et al. |
| 2014/0299815 A1 | 10/2014 | Ueda et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2014/0371701 A1 | 12/2014 | Bianchi |
| 2015/0065975 A1 | 3/2015 | Roe |
| 2015/0065981 A1 | 3/2015 | Roe |
| 2015/0080821 A1 | 3/2015 | Peri et al. |
| 2015/0080837 A1 | 3/2015 | Rosati et al. |
| 2015/0080839 A1 | 3/2015 | Trapp et al. |
| 2015/0173967 A1 | 6/2015 | Kreuzer |
| 2015/0173968 A1 | 6/2015 | Joseph |
| 2015/0250662 A1 | 9/2015 | Isele et al. |
| 2015/0250663 A1 | 9/2015 | Wagner et al. |
| 2015/0273433 A1 | 10/2015 | Nakatsuru et al. |
| 2016/0262953 A1 | 9/2016 | Ehrnsperger et al. |
| 2016/0346139 A1 | 12/2016 | Ehrnsperger et al. |
| 2021/0177670 A1 | 6/2021 | Ehrnsperger et al. |

FOREIGN PATENT DOCUMENTS

| | | |
|---|---|---|
| CN | 1238171 A | 12/1999 |
| CN | 2362468 Y | 2/2000 |
| CN | 1371671 A | 10/2002 |
| CN | 2527254 Y | 12/2002 |
| CN | 2535020 Y | 2/2003 |
| CN | 2548609 Y | 5/2003 |
| CN | 1819811 A | 8/2006 |
| CN | 1939242 A | 4/2007 |
| CN | 101018521 A | 8/2007 |
| CN | 101076358 A | 11/2007 |

(56) References Cited

FOREIGN PATENT DOCUMENTS

| | | | |
|---|---|---|---|
| CN | 101292930 A | 10/2008 |
| CN | 201263750 Y | 7/2009 |
| CN | 101610743 A | 12/2009 |
| CN | 201591689 U | 9/2010 |
| CN | 102014824 A | 4/2011 |
| CN | 201855366 U | 6/2011 |
| CN | 102137647 A | 7/2011 |
| CN | 202397708 U | 8/2012 |
| CN | 102686192 A | 9/2012 |
| DE | 3205931 C2 | 8/1985 |
| DE | 3608114 A1 | 9/1987 |
| DE | 19732499 A1 | 2/1999 |
| DE | 10204937 A1 | 8/2003 |
| DE | 69835602 T2 | 9/2006 |
| EP | 083022 A2 | 7/1983 |
| EP | 0149880 A2 | 7/1985 |
| EP | 0206208 A1 | 12/1986 |
| EP | 209561 B1 | 1/1987 |
| EP | 297411 B1 | 1/1989 |
| EP | 374542 B1 | 6/1990 |
| EP | 0394274 A1 | 10/1990 |
| EP | 0403832 A1 | 12/1990 |
| EP | 481322 B1 | 4/1992 |
| EP | 530438 A1 | 3/1993 |
| EP | 547847 A1 | 6/1993 |
| EP | 555346 B1 | 8/1993 |
| EP | 559476 A1 | 9/1993 |
| EP | 304957 B2 | 4/1994 |
| EP | 591647 B2 | 4/1994 |
| EP | 597273 B1 | 5/1994 |
| EP | 601610 B2 | 6/1994 |
| EP | 632068 A1 | 1/1995 |
| EP | 0640330 A1 | 3/1995 |
| EP | 0668066 A2 | 8/1995 |
| EP | 685214 B1 | 12/1995 |
| EP | 687453 B2 | 12/1995 |
| EP | 0689817 A2 | 1/1996 |
| EP | 0691133 A1 | 1/1996 |
| EP | 0700673 A1 | 3/1996 |
| EP | 394274 B2 | 7/1996 |
| EP | 0724418 A1 | 8/1996 |
| EP | 0725613 A1 | 8/1996 |
| EP | 725615 B1 | 8/1996 |
| EP | 0725616 A1 | 8/1996 |
| EP | 0737055 A1 | 10/1996 |
| EP | 0737056 A1 | 10/1996 |
| EP | 758543 B1 | 2/1997 |
| EP | 0761194 A2 | 3/1997 |
| EP | 769284 B1 | 4/1997 |
| EP | 0778762 A1 | 6/1997 |
| EP | 0781537 A1 | 7/1997 |
| EP | 783877 B1 | 7/1997 |
| EP | 787472 B1 | 8/1997 |
| EP | 788874 B1 | 8/1997 |
| EP | 0790839 A1 | 8/1997 |
| EP | 0796068 A2 | 9/1997 |
| EP | 799004 B1 | 10/1997 |
| EP | 822794 B1 | 2/1998 |
| EP | 826351 B1 | 3/1998 |
| EP | 844861 B1 | 6/1998 |
| EP | 863733 B1 | 9/1998 |
| EP | 971751 A1 | 9/1998 |
| EP | 0875224 A1 | 11/1998 |
| EP | 880955 B1 | 12/1998 |
| EP | 891758 B1 | 1/1999 |
| EP | 0893115 A2 | 1/1999 |
| EP | 724418 B1 | 3/1999 |
| EP | 725613 B1 | 3/1999 |
| EP | 725616 B1 | 3/1999 |
| EP | 904755 B1 | 3/1999 |
| EP | 0916327 A1 | 5/1999 |
| EP | 925769 A2 | 6/1999 |
| EP | 933074 B1 | 8/1999 |
| EP | 937736 A2 | 8/1999 |
| EP | 941157 B1 | 9/1999 |
| EP | 947549 B1 | 10/1999 |
| EP | 951887 B1 | 10/1999 |
| EP | 0951890 A2 | 10/1999 |
| EP | 953326 B1 | 11/1999 |
| EP | 0978263 A1 | 2/2000 |
| EP | 985397 B1 | 3/2000 |
| EP | 0988846 A2 | 3/2000 |
| EP | 1005847 A2 | 6/2000 |
| EP | 1008333 A2 | 6/2000 |
| EP | 1018999 A2 | 7/2000 |
| EP | 1022008 A2 | 7/2000 |
| EP | 1023884 A2 | 8/2000 |
| EP | 1053729 A1 | 11/2000 |
| EP | 1059072 A2 | 12/2000 |
| EP | 1063954 A1 | 1/2001 |
| EP | 1071388 A1 | 1/2001 |
| EP | 1078618 A2 | 2/2001 |
| EP | 1088537 A2 | 4/2001 |
| EP | 752892 B1 | 7/2001 |
| EP | 1116479 A2 | 7/2001 |
| EP | 1132069 A2 | 9/2001 |
| EP | 1173128 A1 | 1/2002 |
| EP | 1184018 A2 | 3/2002 |
| EP | 1199059 A1 | 4/2002 |
| EP | 1199327 A2 | 4/2002 |
| EP | 1208824 A2 | 5/2002 |
| EP | 1210925 A2 | 6/2002 |
| EP | 1224922 A2 | 7/2002 |
| EP | 1225857 A1 | 7/2002 |
| EP | 1253231 A2 | 10/2002 |
| EP | 1262531 A1 | 12/2002 |
| EP | 1275358 A2 | 1/2003 |
| EP | 1275361 A2 | 1/2003 |
| EP | 1293187 A1 | 3/2003 |
| EP | 1339368 A1 | 9/2003 |
| EP | 1374817 A1 | 1/2004 |
| EP | 1388334 A1 | 2/2004 |
| EP | 1402863 A1 | 3/2004 |
| EP | 1403419 A1 | 3/2004 |
| EP | 962208 B1 | 8/2004 |
| EP | 1447066 A1 | 8/2004 |
| EP | 1447067 A1 | 8/2004 |
| EP | 963749 B1 | 11/2004 |
| EP | 1263374 B1 | 11/2004 |
| EP | 1495739 A1 | 1/2005 |
| EP | 1541103 A1 | 6/2005 |
| EP | 1551344 A1 | 7/2005 |
| EP | 1586289 A1 | 10/2005 |
| EP | 1588723 A1 | 10/2005 |
| EP | 1605882 A1 | 12/2005 |
| EP | 1609448 A1 | 12/2005 |
| EP | 1019003 B1 | 1/2006 |
| EP | 1621165 A1 | 2/2006 |
| EP | 1621166 A1 | 2/2006 |
| EP | 1621167 A2 | 2/2006 |
| EP | 1632206 A1 | 3/2006 |
| EP | 1642556 A1 | 4/2006 |
| EP | 1656162 A1 | 5/2006 |
| EP | 1669046 A1 | 6/2006 |
| EP | 1019002 B1 | 8/2006 |
| EP | 1688114 A1 | 8/2006 |
| EP | 1723939 A1 | 11/2006 |
| EP | 1192312 B1 | 12/2006 |
| EP | 1013252 B1 | 1/2007 |
| EP | 1738727 A1 | 1/2007 |
| EP | 1754461 A1 | 2/2007 |
| EP | 1787611 A1 | 5/2007 |
| EP | 1175194 B1 | 6/2007 |
| EP | 1813238 A2 | 8/2007 |
| EP | 1304986 B1 | 11/2007 |
| EP | 1920743 A2 | 5/2008 |
| EP | 1332742 B1 | 6/2008 |
| EP | 2008626 A1 | 12/2008 |
| EP | 2055279 A1 | 5/2009 |
| EP | 2093049 A1 | 8/2009 |
| EP | 2130522 A1 | 12/2009 |
| EP | 2295493 A1 | 3/2011 |
| EP | 2305749 A1 | 4/2011 |
| EP | 2314265 A1 | 4/2011 |

(56) References Cited

FOREIGN PATENT DOCUMENTS

| | | | |
|---|---|---|---|
| EP | 2330152 A1 | 6/2011 |
| EP | 1196122 B2 | 11/2011 |
| EP | 2444045 A1 | 4/2012 |
| EP | 2444046 A1 | 4/2012 |
| EP | 2486905 A1 | 8/2012 |
| EP | 2532328 A1 | 12/2012 |
| EP | 2532332 A1 | 12/2012 |
| EP | 2656826 A1 | 10/2013 |
| EP | 2679210 A1 | 1/2014 |
| EP | 2740449 A1 | 6/2014 |
| EP | 2740450 A1 | 6/2014 |
| EP | 2740452 A1 | 6/2014 |
| EP | 2786731 A1 | 10/2014 |
| ES | 2213491 A1 | 8/2004 |
| FR | 2566631 A1 | 1/1986 |
| FR | 2583377 A1 | 12/1986 |
| FR | 2612770 A1 | 9/1988 |
| FR | 2699813 A1 | 7/1994 |
| FR | 2810234 A1 | 12/2001 |
| GB | 1307441 A | 2/1973 |
| GB | 1333081 A | 10/1973 |
| GB | 1513055 A | 6/1978 |
| GB | 2101468 A | 1/1983 |
| GB | 2170108 A | 7/1986 |
| GB | 2262873 A | 7/1993 |
| GB | 2288540 A | 10/1995 |
| GB | 2354449 A | 3/2001 |
| GB | 2452260 A | 3/2009 |
| GR | 851769 B | 11/1985 |
| IN | 0984KOL1999 | 10/2005 |
| IN | 212479 | 3/2007 |
| IN | 208543 | 8/2007 |
| IN | 0980MUM2009 | 6/2009 |
| JP | 598322 U | 1/1984 |
| JP | 63148323 U | 9/1988 |
| JP | 2107250 A | 4/1990 |
| JP | 03224481 B2 | 10/1991 |
| JP | 04122256 A | 4/1992 |
| JP | 04341368 A | 11/1992 |
| JP | 06191505 A | 7/1994 |
| JP | 06269475 A | 9/1994 |
| JP | 07124193 A | 5/1995 |
| JP | 08215629 A | 8/1996 |
| JP | H10295728 A | 11/1998 |
| JP | 10328232 A | 12/1998 |
| JP | 11033056 A | 2/1999 |
| JP | 11318980 A | 11/1999 |
| JP | 11320742 A | 11/1999 |
| JP | 2000232985 A | 8/2000 |
| JP | 2000238161 A | 9/2000 |
| JP | 2001037810 A | 2/2001 |
| JP | 2001046435 A | 2/2001 |
| JP | 2001120597 A | 5/2001 |
| JP | 2001158074 A | 6/2001 |
| JP | 2001178768 A | 7/2001 |
| JP | 2001198157 A | 7/2001 |
| JP | 2001224626 A | 8/2001 |
| JP | 2001258935 A | 9/2001 |
| JP | 3224481 | 10/2001 |
| JP | 2001277394 A | 10/2001 |
| JP | 2001301857 A | 10/2001 |
| JP | 03420481 B2 | 11/2001 |
| JP | 2001321397 A | 11/2001 |
| JP | 2001353174 A | 12/2001 |
| JP | 2002052042 A | 2/2002 |
| JP | 2002065718 A | 3/2002 |
| JP | 2002113800 A | 4/2002 |
| JP | 2002165832 A | 6/2002 |
| JP | 2002165836 A | 6/2002 |
| JP | 2002178429 A | 6/2002 |
| JP | 2002272769 A | 9/2002 |
| JP | 2002320641 A | 11/2002 |
| JP | 2002325792 A | 11/2002 |
| JP | 2002325799 A | 11/2002 |
| JP | 2002369841 A | 12/2002 |
| JP | 2003153955 A | 5/2003 |
| JP | 2003265523 A | 9/2003 |
| JP | 2003265524 A | 9/2003 |
| JP | 2003275237 A | 9/2003 |
| JP | 2003325563 A | 11/2003 |
| JP | 2004065930 A | 3/2004 |
| JP | 2004089269 A | 3/2004 |
| JP | 03566012 B2 | 6/2004 |
| JP | 03568146 B2 | 6/2004 |
| JP | 2004222868 A | 8/2004 |
| JP | 2004337314 A | 12/2004 |
| JP | 2004337385 A | 12/2004 |
| JP | 2004350864 A | 12/2004 |
| JP | 2005000312 A | 1/2005 |
| JP | 03616077 B2 | 2/2005 |
| JP | 03640475 B2 | 4/2005 |
| JP | 2005118339 A | 5/2005 |
| JP | 03660816 B2 | 6/2005 |
| JP | 03676219 B2 | 7/2005 |
| JP | 03688403 B2 | 8/2005 |
| JP | 03705943 B2 | 10/2005 |
| JP | 03719819 B2 | 11/2005 |
| JP | 03724963 B2 | 12/2005 |
| JP | 03725008 B2 | 12/2005 |
| JP | 03737376 B2 | 1/2006 |
| JP | 2006014792 A | 1/2006 |
| JP | 2006110329 A | 4/2006 |
| JP | 2006513824 A | 4/2006 |
| JP | 03781617 B2 | 5/2006 |
| JP | 2006116036 A | 5/2006 |
| JP | 03801449 B2 | 7/2006 |
| JP | 03850102 B2 | 11/2006 |
| JP | 03850207 B2 | 11/2006 |
| JP | 03856941 B2 | 12/2006 |
| JP | 2006325639 A | 12/2006 |
| JP | 2006346021 A | 12/2006 |
| JP | 03868628 B2 | 1/2007 |
| JP | 03874499 B2 | 1/2007 |
| JP | 2007007455 A | 1/2007 |
| JP | 2007007456 A | 1/2007 |
| JP | 03877702 B2 | 2/2007 |
| JP | 2007089906 A | 4/2007 |
| JP | 2007105198 A | 4/2007 |
| JP | 2007130504 A | 5/2007 |
| JP | 03926042 B2 | 6/2007 |
| JP | 03934855 B2 | 6/2007 |
| JP | 2007152033 A | 6/2007 |
| JP | 03986210 B2 | 7/2007 |
| JP | 03986222 B2 | 7/2007 |
| JP | 2007167453 A | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 03904356 B2 | 11/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 4177770 B2 | 8/2008 |
| JP | 04190675 B2 | 9/2008 |
| JP | 04190693 B2 | 9/2008 |
| JP | 04208338 B2 | 10/2008 |
| JP | 2008246089 A | 10/2008 |
| JP | 04230971 B2 | 12/2008 |

(56) References Cited

FOREIGN PATENT DOCUMENTS

| | | |
|---|---|---|
| JP | 2008295475 A | 12/2008 |
| JP | 2008295713 A | 12/2008 |
| JP | 04261593 B2 | 2/2009 |
| JP | 2009028186 A | 2/2009 |
| JP | 2009082481 A | 4/2009 |
| JP | 2009112590 A | 5/2009 |
| JP | 2009136601 A | 6/2009 |
| JP | 2009142401 A | 7/2009 |
| JP | 04322228 B2 | 8/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 A | 1/2010 |
| JP | 04458702 B2 | 2/2010 |
| JP | 04459013 B2 | 2/2010 |
| JP | 2010022560 A | 2/2010 |
| JP | 04481325 B2 | 3/2010 |
| JP | 2010046155 A | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010099531 A | 5/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 A | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 4577766 B2 | 9/2010 |
| JP | 04587947 B2 | 9/2010 |
| JP | 2010194124 A | 9/2010 |
| JP | 2010194218 A | 9/2010 |
| JP | 2010201093 A | 9/2010 |
| JP | 2010221067 A | 10/2010 |
| JP | 2010227387 A | 10/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 A | 2/2011 |
| JP | 04693574 B2 | 3/2011 |
| JP | 2011067484 A | 4/2011 |
| JP | 2011072451 A | 4/2011 |
| JP | 2011072720 A | 4/2011 |
| JP | 2011104014 A | 6/2011 |
| JP | 2011104122 A | 6/2011 |
| JP | 2011120661 A | 6/2011 |
| JP | 2011125360 A | 6/2011 |
| JP | 2011125537 A | 6/2011 |
| JP | 2011518613 A | 6/2011 |
| JP | 04776516 B2 | 7/2011 |
| JP | 2011130797 A | 7/2011 |
| JP | 2011130799 A | 7/2011 |
| JP | 2011156031 A | 8/2011 |
| JP | 2011156032 A | 8/2011 |
| JP | 2011156070 A | 8/2011 |
| JP | 2011156254 A | 8/2011 |
| JP | 04824882 B2 | 9/2011 |
| JP | 4850272 B2 | 10/2011 |
| JP | 04855533 B2 | 11/2011 |
| JP | 2011239858 A | 12/2011 |
| JP | 2011240050 A | 12/2011 |
| JP | 2012500669 A | 1/2012 |
| JP | 04931572 B2 | 2/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 04937225 B2 | 5/2012 |
| JP | 2012100886 A | 5/2012 |
| JP | 05016020 B2 | 6/2012 |
| JP | 05027364 B2 | 6/2012 |
| JP | 5715806 B2 | 6/2012 |
| JP | 2012115378 A | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125452 A | 7/2012 |
| JP | 2012125625 A | 7/2012 |
| JP | 2012130736 A | 7/2012 |
| JP | 05053765 B2 | 8/2012 |
| JP | 05070275 B2 | 8/2012 |
| JP | 2012152482 A | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 2012179230 A | 9/2012 |
| JP | 2012179286 A | 9/2012 |
| JP | 05113146 B2 | 10/2012 |
| JP | 2012205924 A | 10/2012 |
| JP | 05129536 B2 | 11/2012 |
| JP | 2012223230 A | 11/2012 |
| JP | 2012223231 A | 11/2012 |
| JP | 05105884 B2 | 12/2012 |
| JP | 5291238 B1 | 6/2013 |
| JP | 2014515973 A | 7/2014 |
| JP | 2014534820 A | 12/2014 |
| JP | 2016502870 A | 2/2016 |
| KR | 20010005620 A | 1/2001 |
| KR | 20020035634 A | 5/2002 |
| KR | 20080028771 A | 4/2008 |
| SE | 9400916 | 3/1994 |
| SE | 9704893 | 12/1997 |
| WO | 9015830 A1 | 12/1990 |
| WO | 9219198 A1 | 11/1992 |
| WO | 9321237 A1 | 10/1993 |
| WO | 9321879 A1 | 11/1993 |
| WO | 9514453 A2 | 6/1995 |
| WO | 9515139 A1 | 6/1995 |
| WO | 9516424 A1 | 6/1995 |
| WO | 9516746 A1 | 6/1995 |
| WO | 9519753 A1 | 7/1995 |
| WO | 9521596 A1 | 8/1995 |
| WO | 9524173 A2 | 9/1995 |
| WO | 9526209 A1 | 10/1995 |
| WO | 9529657 A1 | 11/1995 |
| WO | 9532698 A1 | 12/1995 |
| WO | 9534329 A1 | 12/1995 |
| WO | 9616624 A2 | 6/1996 |
| WO | 9619173 A1 | 6/1996 |
| WO | 96029967 A1 | 10/1996 |
| WO | 9711659 A1 | 4/1997 |
| WO | 9717922 A1 | 5/1997 |
| WO | 9724096 A1 | 7/1997 |
| WO | 9816179 A1 | 4/1998 |
| WO | 9816180 A1 | 4/1998 |
| WO | 9843684 A1 | 10/1998 |
| WO | 9913813 A1 | 3/1999 |
| WO | 9934841 A1 | 7/1999 |

(56) References Cited

FOREIGN PATENT DOCUMENTS

| | | |
|---|---|---|
| WO | 9951178 A1 | 10/1999 |
| WO | 200000235 A1 | 1/2000 |
| WO | 200032145 A1 | 6/2000 |
| WO | 200059430 A1 | 10/2000 |
| WO | 200115647 A1 | 3/2001 |
| WO | 200126596 A1 | 4/2001 |
| WO | 0135886 A1 | 5/2001 |
| WO | 200207663 A1 | 1/2002 |
| WO | 200232962 A2 | 4/2002 |
| WO | 0236059 A1 | 5/2002 |
| WO | 2002064877 A2 | 8/2002 |
| WO | 2002067809 A2 | 9/2002 |
| WO | 2003009794 A2 | 2/2003 |
| WO | 2003039402 A2 | 5/2003 |
| WO | 2003053297 A2 | 7/2003 |
| WO | 03079946 A2 | 10/2003 |
| WO | 03101622 A2 | 12/2003 |
| WO | 2003105738 A1 | 12/2003 |
| WO | 2004021946 A1 | 3/2004 |
| WO | 2004049995 A1 | 6/2004 |
| WO | 2004071539 A2 | 8/2004 |
| WO | 2004084784 A1 | 10/2004 |
| WO | 2004105664 A1 | 12/2004 |
| WO | 2005018694 A1 | 3/2005 |
| WO | 2005087164 A1 | 9/2005 |
| WO | 2005102237 A1 | 11/2005 |
| WO | 2006015138 A1 | 2/2006 |
| WO | 2006059922 A1 | 6/2006 |
| WO | 2006062258 A2 | 6/2006 |
| WO | 2006066029 A1 | 6/2006 |
| WO | 2006083584 A2 | 8/2006 |
| WO | 2006104024 A1 | 10/2006 |
| WO | 2006134904 A1 | 12/2006 |
| WO | 2006134906 A1 | 12/2006 |
| WO | 2007000315 A1 | 1/2007 |
| WO | 2007046052 A1 | 4/2007 |
| WO | 2007047598 A1 | 4/2007 |
| WO | 2007049725 A1 | 5/2007 |
| WO | 2007061035 A1 | 5/2007 |
| WO | 2007141744 A1 | 12/2007 |
| WO | 2007142145 A1 | 12/2007 |
| WO | 2007148502 A1 | 12/2007 |
| WO | 2008018922 A1 | 2/2008 |
| WO | 2008065945 A1 | 6/2008 |
| WO | 2008146749 A1 | 12/2008 |
| WO | 2008155699 A1 | 12/2008 |
| WO | 2009004941 A1 | 1/2009 |
| WO | 2009005114 A1 | 1/2009 |
| WO | 2009005431 A1 | 1/2009 |
| WO | 2009041223 A2 | 4/2009 |
| WO | 2009096108 A1 | 8/2009 |
| WO | 2009107435 A1 | 9/2009 |
| WO | 2009122830 A1 | 10/2009 |
| WO | 2009134626 A1 | 11/2009 |
| WO | 2009139255 A1 | 11/2009 |
| WO | 2009152018 A1 | 12/2009 |
| WO | 2009155264 A2 | 12/2009 |
| WO | 2009155265 A2 | 12/2009 |
| WO | 2010027719 A2 | 3/2010 |
| WO | 2010071508 A1 | 6/2010 |
| WO | 2010074319 A1 | 7/2010 |
| WO | 2010107096 A1 | 9/2010 |
| WO | 2010114052 A1 | 10/2010 |
| WO | 2010117015 A1 | 10/2010 |
| WO | 2010118272 A1 | 10/2010 |
| WO | 201153044 A2 | 5/2011 |
| WO | 2011080858 A1 | 7/2011 |
| WO | 2011118725 A1 | 9/2011 |
| WO | 2011118842 A1 | 9/2011 |
| WO | 2011145653 A1 | 11/2011 |
| WO | 2011150955 A1 | 12/2011 |
| WO | 2011163582 A1 | 12/2011 |
| WO | 2012002252 A1 | 1/2012 |
| WO | 2012014436 A1 | 2/2012 |
| WO | 2012035787 A1 | 3/2012 |
| WO | 2012042908 A1 | 4/2012 |
| WO | 2012043077 A1 | 4/2012 |
| WO | 2012043078 A1 | 4/2012 |
| WO | 2012043082 A1 | 4/2012 |
| WO | 2012048878 A1 | 4/2012 |
| WO | 2012048879 A1 | 4/2012 |
| WO | 2012052172 A1 | 4/2012 |
| WO | 2012067216 A1 | 5/2012 |
| WO | 2012073499 A1 | 6/2012 |
| WO | 2012074466 A1 | 6/2012 |
| WO | 201291016 A1 | 7/2012 |
| WO | 2012090508 A1 | 7/2012 |
| WO | 2012101934 A1 | 8/2012 |
| WO | 2012102034 A1 | 8/2012 |
| WO | 2012117764 A1 | 9/2012 |
| WO | 2012117824 A1 | 9/2012 |
| WO | 2012132460 A1 | 10/2012 |
| WO | 2012165327 A1 | 12/2012 |
| WO | 2012170778 A1 | 12/2012 |
| WO | 2012170779 A1 | 12/2012 |
| WO | 2012170781 A1 | 12/2012 |
| WO | 2012170783 A1 | 12/2012 |
| WO | 2012170808 A1 | 12/2012 |
| WO | 2012174026 A1 | 12/2012 |
| WO | 2012177400 A1 | 12/2012 |
| WO | 2013001788 A1 | 1/2013 |
| WO | 2013021651 A1 | 2/2013 |
| WO | 2013046701 A1 | 4/2013 |
| WO | 2013047268 A1 | 4/2013 |
| WO | 2013056978 A2 | 4/2013 |
| WO | 2013060733 A1 | 5/2013 |
| WO | 2013061867 A1 | 5/2013 |
| WO | 2013077074 A1 | 5/2013 |
| WO | 2014073636 A1 | 5/2014 |
| WO | 2014078247 A2 | 5/2014 |
| WO | 2014170859 A1 | 10/2014 |
| WO | 20140203751 | 12/2014 |
| WO | 2015005502 A2 | 1/2015 |
| WO | 2015095514 A2 | 6/2015 |
| WO | 2016040091 A1 | 3/2016 |

OTHER PUBLICATIONS

All Office Actions, U.S. Appl. No. 14/100,059.
All Office Actions, U.S. Appl. No. 15/236,548.
PCT Search Report and Written Opinion for PCT/US2013/074065 dated Mar. 17, 2014, 17 pages.
Extended European Search Report and Search Opinion; Application No. 12196341.7 dated Apr. 3, 2013; 11 pages.
All Office Actions, U.S. Appl. No. 15/161,331.
All Office Actions, U.S. Appl. No. 14/540,079.
All Office Actions, U.S. Appl. No. 17/184,762.
All Office Actions; U.S. Appl. No. 15/959,568, filed Apr. 23, 2018.
Tonjours Product, photos of packaging and product, 5 pages.

\* cited by examiner

ABSORBENT ARTICLE WITH HIGH ABSORBENT MATERIAL CONTENT

CROSS REFERENCE TO RELATED APPLICATIONS

This application is a continuation of, and claims priority under 35 U.S.C. § 120 to, U.S. patent application Ser. No. 17/184,762, filed Feb. 25, 2021, which is a continuation of U.S. patent application Ser. No. 15/959,568, filed Apr. 23, 2018 (now granted U.S. Pat. No 10,966,885, issued Apr. 6, 2021), which is a continuation of U.S. patent application Ser. No. 15/236,548, filed Aug. 15, 2016, which is a continuation of U.S. patent application Ser. No. 15/161,331, filed May 23, 2016, which is a continuation of U.S. patent application Ser. No. 14/540,079, filed Nov. 13, 2014 (now granted U.S. Pat. No. 9,375,358, issued Jun. 28, 2016), which is a continuation of U.S. patent application Ser. No. 14/100,059, filed Dec. 9, 2013 (now granted U.S. Pat. No. 10,022,280 issued Jul. 17, 2018), which claims priority, under 35 U.S.C. § 119(b) to European Patent Application No. EP 12196341.7, filed Dec. 10, 2012, the substances of each of which is incorporated herein by reference.

FIELD OF THE INVENTION

The invention provides an absorbent article for personal hygiene such as a baby diaper, a training pant or an adult incontinence product.

BACKGROUND OF THE INVENTION

Absorbent articles for personal hygiene, such as disposable diapers for infants, training pants for toddlers or adult incontinence undergarments are designed to absorb and contain body exudates, in particular large quantity of urine. These absorbent articles comprise several layers providing different functions, for example a topsheet, a backsheet and in-between an absorbent core, among other layers.

The function of the absorbent core is to absorb and retain the exudates for a prolonged amount of time, for example overnight for a diaper, minimize re-wet to keep the wearer dry and avoid soiling of clothes or bed sheets. The majority of currently marketed absorbent articles comprise as absorbent material a blend of comminuted wood pulp with superabsorbent polymers (SAP) in particulate form, also called absorbent gelling materials (AGM), see for example U.S. Pat. No. 5,151,092 (Buell). Absorbent articles having a core consisting essentially of SAP as absorbent material (so called "airfelt-free" cores) have also been proposed but are less common than traditional mixed cores (see e.g. WO2008/155699 (Hundorf), WO95/11652 (Tanzer), WO2012/052172 (Van Malderen)).

Absorbent articles comprising a core with slits or grooves have also been proposed, typically to increase the fluid acquisition properties of the core WO95/11652 (Tanzer) discloses absorbent articles which include superabsorbent material located in discrete pockets having water-sensitive and water-insensitive containment structure. WO2009/047596 (Wright) discloses an absorbent article with a slit absorbent core.

These absorbent articles may typically comprise leg cuffs which provide improved containment of liquids and other body exudates. Leg cuffs may also be referred to as leg bands, side flaps, barrier cuffs, or elastic cuffs. Usually each leg cuff will comprise one or more elastic string or element comprised in the chassis of the diaper for example between the topsheet and backsheet in the area of the leg openings to provide an effective seal while the diaper is in use. These elasticized elements which are substantially planar with the chassis of the absorbent article will be referred to herein as gasketing cuffs. It is also usual for the leg cuffs to comprise raised elasticized flaps, herein referred to as barrier leg cuffs, which improve the containment of fluid in the leg-torso joint regions. Each barrier leg cuff typically comprises one or more elastic strings. U.S. Pat. Nos. 4,808,178 and 4,909,803 (Aziz) describe disposable diapers having such raised elasticized flaps. U.S. Pat. No. 4,695,278 (Lawson) and U.S. Pat. No. 4,795,454 (Dragoo) describe disposable diapers having dual cuffs, including gasketing cuffs and barrier leg cuffs. U.S. Pat. No. 4,704,116 (Enloe) discloses an absorbent garment comprising a pair of gasketing cuffs and a pair of barrier leg cuffs which attached to or formed from the topsheet and spaced inwardly from said elasticized leg openings, defining a waste-containment pocket.

Absorbent articles generally have a high absorbent capacity and the absorbent core can expand to several times its weight and volume. These increases will typically cause the absorbent articles to sag in the crotch region as it becomes saturated with liquid, which may cause the barrier cuffs to partially lose contact with the wearer's skin. This can lead to a loss of functionality of the barrier cuffs, with the increased possibly of leakage.

US2007/088308 (Ehrnsperger) addresses this problem by suggesting a barrier cuff strip which extends longitudinally from front to back waist regions along the topsheet and includes front and back ends and proximal and distal edges connecting the front and back ends. The distal edge is attached at a cuff end bond region having an outer bond edge and an inner bond edge spaced longitudinally from the outer bond edge. A longitudinal distance from the inner bond edge to the laterally extending side at the one of the front and back waist regions is about ½ or more of a longitudinal length of the front or back waist regions.

US2004/220541 (Suzuki) discloses an absorbent sheet having concave and convex portions on its surface and spontaneously exhibiting a three-dimensional structure in that a concave-convex structure is formed. US2007/244455 (Hansson) discloses an absorbent core in an absorbent article provided with at least two folding guides extending in a substantially longitudinal direction in the crotch region and dividing at least a part of the crotch region of the absorbent core in a central portion and two lateral portions as seen in a transverse direction. At least two stretchable crotch elastic members are arranged in the crotch portion of the article and are attached to the absorbent core and/or to the inner or outer cover.

Although the prior art has provided different solutions to the problem of improving leakage prevention, it still beneficial to develop new and improved solution to provide better fit of the leg cuffs at high load. The present inventors have found that it may be beneficial for the free edges of the barrier leg cuffs to follow the fold lines between legs and torso. These fold lines are a very good position for the raised edge of the barrier leg cuffs to follow because of (a) it is a low motion area, and (b) it is in a region closest to the body. These anatomical fold lines are not straight, but rather the distance between the left and right fold line is larger in the front and back than in the crotch.

The inventors have found that when the width of the diaper between the barrier leg cuffs in the crotch portion is reduced as indicated further below, the barrier leg cuff's free edge can better follow the curved fold lines as the article becomes loaded which improves leakage prevention. This is particularly advantageous as the leakage prevention is thus increased when the article becomes highly loaded and thus when the leakage prevention is most needed. The inventors have found that this effect was particularly present when the absorbent core contains high proportions of superabsorbent polymers and at least partially longitudinally extending channels.

SUMMARY OF THE INVENTION

The invention provides an absorbent article for personal hygiene such as a diaper or training pant having a front edge and a back edge. The absorbent article comprises a front region, a back region, a crotch region disposed between the front region and the back region, and a longitudinal axis extending in a longitudinal direction of the article. The article further includes a liquid permeable topsheet; a liquid impermeable backsheet; and an absorbent core disposed between the topsheet and backsheet. The absorbent core comprising a combination of superabsorbent polymer and cellulose fibers. At least one channel is positioned within a layer located between the topsheet and the backsheet, and longitudinally-extending within a portion of the front region and the crotch region, the at least one channel being substantially free of fibers and superabsorbent polymer. An indentation occurs in at least one of the topsheet and the backsheet that corresponds to the at least one channel when the article is loaded with fluid. The article may further comprise an acquisition-distribution layer and/or a waist feature.

DETAILED DESCRIPTION OF THE INVENTION

Introduction

Figure 1:
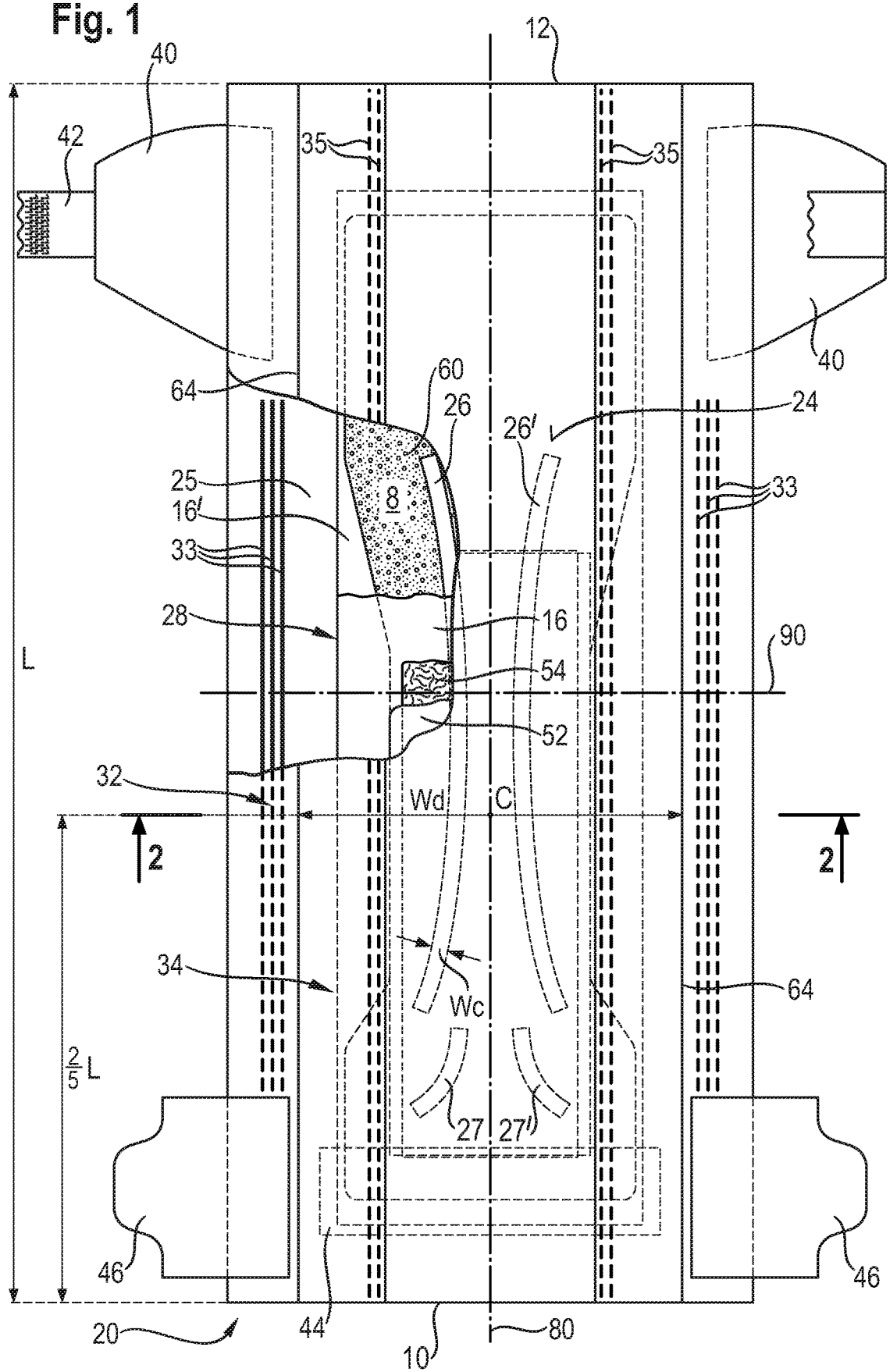
FIG. 1 is a top view of an embodiment of the present invention in the form of a diaper with some layers partially removed.

As used herein, the term "absorbent article" refers to disposable devices such as infant or adult diapers, training pants, and the like which are placed against or in proximity to the body of the wearer to absorb and contain the various exudates discharged from the body. Typically these articles comprise a topsheet, backsheet, an absorbent core and optionally an acquisition system (which may be comprised of one or several layers) and typically other components, with the absorbent core normally placed between the backsheet and the acquisition system or topsheet.

The absorbent articles of the invention will be further illustrated in the below description and in the Figures in the form of a taped diaper. Nothing in this description should be however considered limiting the scope of the claims unless explicitly indicated otherwise. Unless indicated otherwise, the description refers to the dry article, i.e. before use and conditioned at least 24 hours at 21° C.+/−2° C. and 50+/−20% Relative Humidity (RH).

A "nonwoven web" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0 2 mm and they come in several different forms such as short fibers (known as staple, or chopped), continuous single fibers (filaments or monofilaments), untwisted bundles of continuous filaments (tow), and twisted bundles of continuous filaments (yam). Nonwoven webs can be formed by many processes such as meltblowing, spunbonding, solvent spinning, electrospinning, carding and airlaying. The basis weight of nonwoven webs is usually expressed in grams per square meter (g/m$^2$ or gsm).

The term "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

General Description of the Absorbent Article

Figure 2:
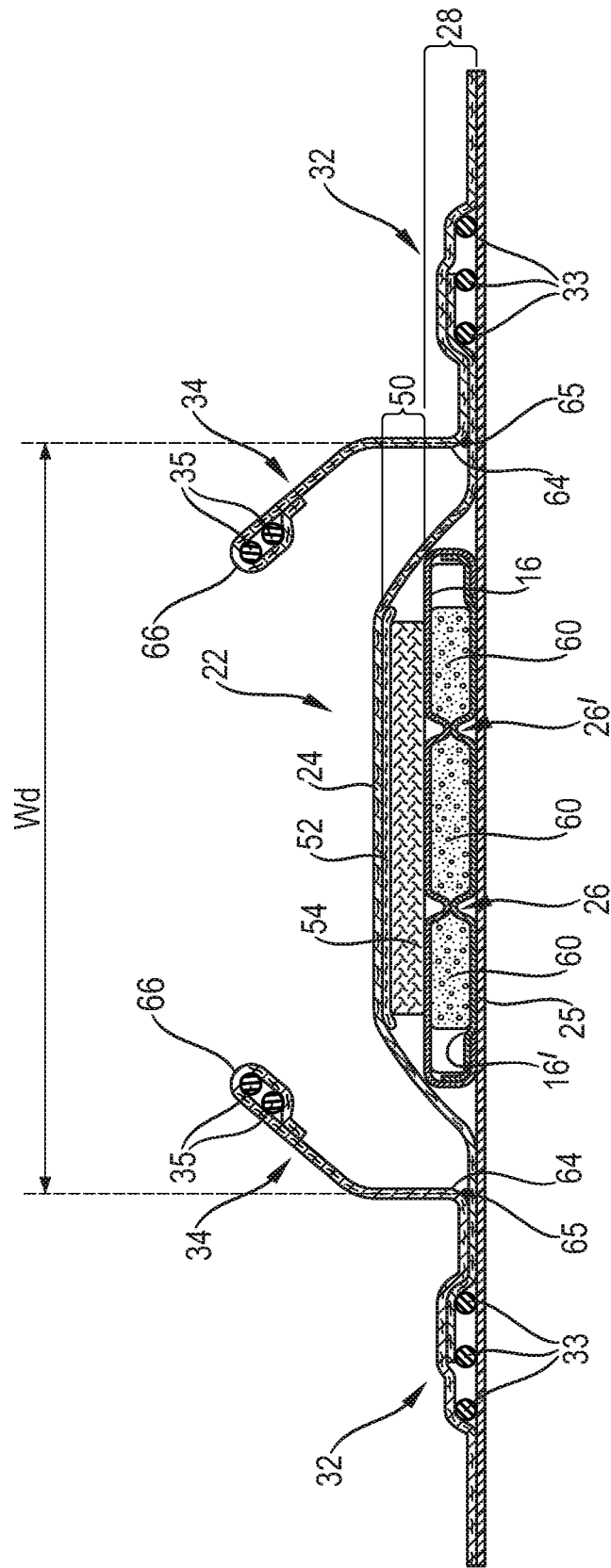
FIG. 2 is a transversal cross-section of the embodiment of FIG. 1 at the crotch point.
Figure 3:
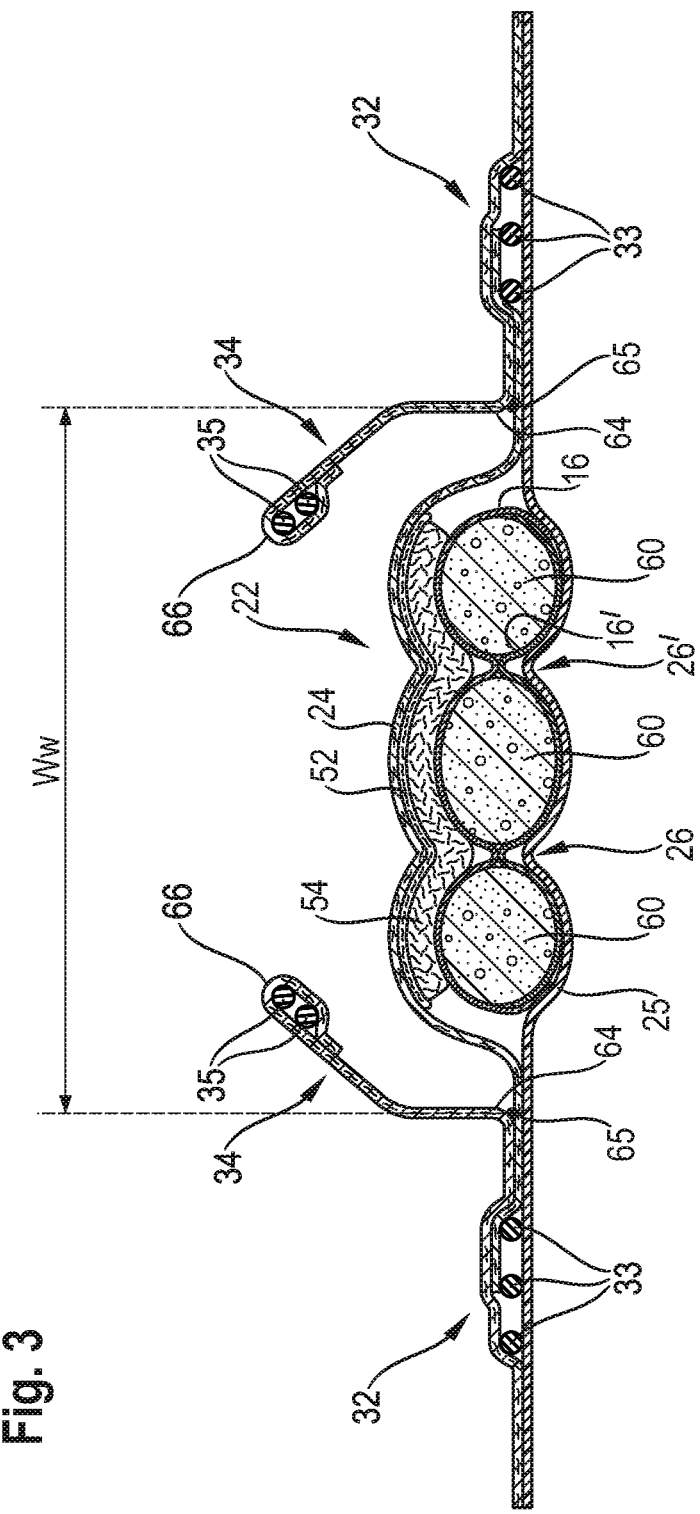
FIG. 3 is a transversal cross-section of the embodiment of FIG. 1 taken at the same point as FIG. 2 where the diaper has been loaded with fluid.

An exemplary absorbent article according to the invention in the form of an infant diaper 20 is represented in FIGS. 1-3. FIG. 1 is a plan view of the exemplary diaper 20, in a flattened state, with portions of the structure being cut-away to more clearly show the construction of the diaper 20. This diaper 20 is shown for illustration purpose only as the invention may be used for making a wide variety of diapers or other absorbent articles.

The absorbent article comprises a liquid permeable topsheet 24, a liquid impermeable backsheet 25, an absorbent core 28 between the topsheet 24 and the backsheet 25, and barrier leg cuffs 34. The absorbent article may also comprise an acquisition-distribution system ("ADS"), which in the example represented comprises a distribution layer 54 and an acquisition layer 52, which will be further detailed in the following. The article may also comprise elasticized gasketing cuffs 32 joined to the chassis of the absorbent article, typically via the topsheet and/or backsheet, and substantially planar with the chassis of the diaper.

The Figures also show typical taped diaper components such as a fastening system comprising adhesive tabs 42 attached towards the back edge of the article and cooperating with a landing zone 44 on the front of the article. The absorbent article may also comprise other typical elements, which are not represented, such as a back elastic waist feature, a front elastic waist feature, transverse barrier cuff(s), a lotion application, etc. . . . .

The absorbent article 20 comprises a front edge 10, a back edge 12, and two side edges. The front edge 10 is the edge of the article which is intended to be placed towards the front of the user when worn, and the back edge 12 is the opposite edge. In a taped diapers, as exemplarily shown in FIG. 1, the back edge of the diaper is typically on the side of the diaper that comprises the fastening tabs 42 and the front edge is typically on the side of the diaper that comprise the matching landing zone 44. More generally, the front of the article has typically more absorbent capacity than the back of the article. The absorbent article may be notionally divided by a longitudinal axis 80 extending from the front edge to the back edge of the article and dividing the article in two substantially symmetrical halves relative to this axis, with article placed flat and viewed from above as in FIG. 1. The length L of the article can be measured along the longitudinal axis 80 from front edge 10 to back edge 12. The article comprises a crotch point C defined herein as the point placed on the longitudinal axis at a distance of two fifth (⅖) of L starting from the front edge 10 of the article 20.

The crotch region can be defined as the region of the diaper longitudinally centered at the crotch point C and extending towards the front and towards the back of the absorbent article by a distance of one fifth of L (L/5) in each direction for a total length of ⅖ of L. A front region and a back region can be defined as the remaining portions of the diapers placed respectively towards the front and the back edges of the article.

The topsheet 24, the backsheet 25, the absorbent core 28 and the other article components may be assembled in a variety of well known configurations, in particular by gluing or heat embossing. Exemplary diaper configurations are described generally in U.S. Pat. Nos. 3,860,003, 5,221,274, 5,554,145, 5,569,234, 5,580,411, and 6,004,306. The absorbent article is preferably thin. The caliper at the crotch point C of the article may be for example from 4.0 mm to 12.0 mm, in particular from 6.0 mm to 10.0 mm, as measured with the Caliper Test described herein.

The absorbent core 28 comprises absorbent material comprising at least 80% by weight of superabsorbent polymers and a core wrap enclosing the absorbent material. The core wrap may typically comprise two substrates 16 and 16' for the top side and bottom side of the core. The core further comprises at least one channel, represented in FIG. 1 as the four channels 26, 26' and 27, 27'.

These and other components of the articles will now be discussed in more details.

Topsheet 24

The topsheet 24 is the part of the absorbent article that is directly in contact with the wearer's skin. The topsheet 24 can be joined to the backsheet 25, the core 28 and/or any other layers as is known in the art. Usually, the topsheet 24 and the backsheet 25 are joined directly to each other in some locations (e.g. on or close to the periphery of the article) and are indirectly joined together in other locations by directly joining them to one or more other elements of the article 20.

The topsheet 24 is preferably compliant, soft-feeling, and non-irritating to the wearer's skin. Further, at least a portion of the topsheet 24 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, MA under the designation P-8.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643 issued to Curro et al. Such formed films are available from The Procter & Gamble Company of Cincinnati, Ohio as "DRI-WEAVE" and from Tredegar Corporation, based in Richmond, VA, as "CLIFF-T".

Any portion of the topsheet 24 may be coated with a lotion as is known in the art. Examples of suitable lotions include those described in U.S. Pat. Nos. 5,607,760, 5,609, 587, 5,643,588, 5,968,025 and 6,716,441. The topsheet 24 may also include or be treated with antibacterial agents, some examples of which are disclosed in PCT Publication WO95/24173. Further, the topsheet 24, the backsheet 25 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504, assigned to BBA NONWOVENS SIMPSONVILLE. WO2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Typical diaper topsheets have a basis weight of from about 10 to about 21 gsm, in particular between from about 12 to about 18 gsm but other basis weights are possible.

Backsheet 25

The backsheet 25 is generally that portion of the article 20 positioned adjacent the garment-facing surface of the absorbent core 28 and which prevents the exudates absorbed and contained therein from soiling articles such as bedsheets and undergarments. The backsheet 25 is typically impermeable to liquids (e.g. urine). The backsheet may for example be or comprise a thin plastic film such as a thermoplastic film having a thickness of about 0.012 mm to about 0.051 mm Exemplary backsheet films include those manufactured by Tredegar Corporation, based in Richmond, VA, and sold under the trade name CPC2 film. Other suitable backsheet materials may include breathable materials which permit vapors to escape from the diaper 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, VA, and sold under the designation EXAIRE, and monolithic films such as manufactured by Clopay Corporation, Cincinnati, OH under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 25 may be joined to the topsheet 24, the absorbent core 28 or any other element of the diaper 20 by any attachment means known in the art. Suitable attachment means are described above with respect to means for joining the topsheet 24 to other elements of the article 20. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785,996; and 4,842,666. Adhesives which have been found to be satisfactory are manufactured by H. B. Fuller Company of St. Paul, Minnesota and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Absorbent Core 28

As used herein, the term "absorbent core" refers to the individual component of the article having the most absorbent capacity and comprising an absorbent material and a core wrap enclosing the absorbent material. The term "absorbent core" does not include the acquisition-distribution system or layer or any other component of the article which is not either integral part of the core wrap or placed within the core wrap. The core may consist essentially of, or consist of, a core wrap, absorbent material as defined below and glue enclosed within the core wrap.

The absorbent core 28 of the invention comprises absorbent material with a high amount of superabsorbent polymers (herein abbreviated as "SAP") enclosed within a core wrap. The SAP content represents at least 80% by weight of the absorbent material contained in the core wrap. The core wrap is not considered as absorbent material for the purpose of assessing the percentage of SAP in the absorbent core.

By "absorbent material" it is meant a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95% and even up to and including 100% of the weight of the absorbent material contained within the core wrap. This provides a relatively thin core compared to conventional core typically comprising between 40-60% SAP and high content of cellulose fibers. The absorbent material may in particular comprises less than 10% weight percent of natural or synthetic fibers, or less than 5% weight percent, or even be substantially free of natural and/or synthetic fibers. The absorbent material may advantageously comprise little or no airfelt (cellulose) fibers, in particular the absorbent core may comprise less than 15%, 10%, 5% airfelt (cellulose) fibers by weight of the absorbent core, or even be substantially free of cellulose fibers.

Figure 4:
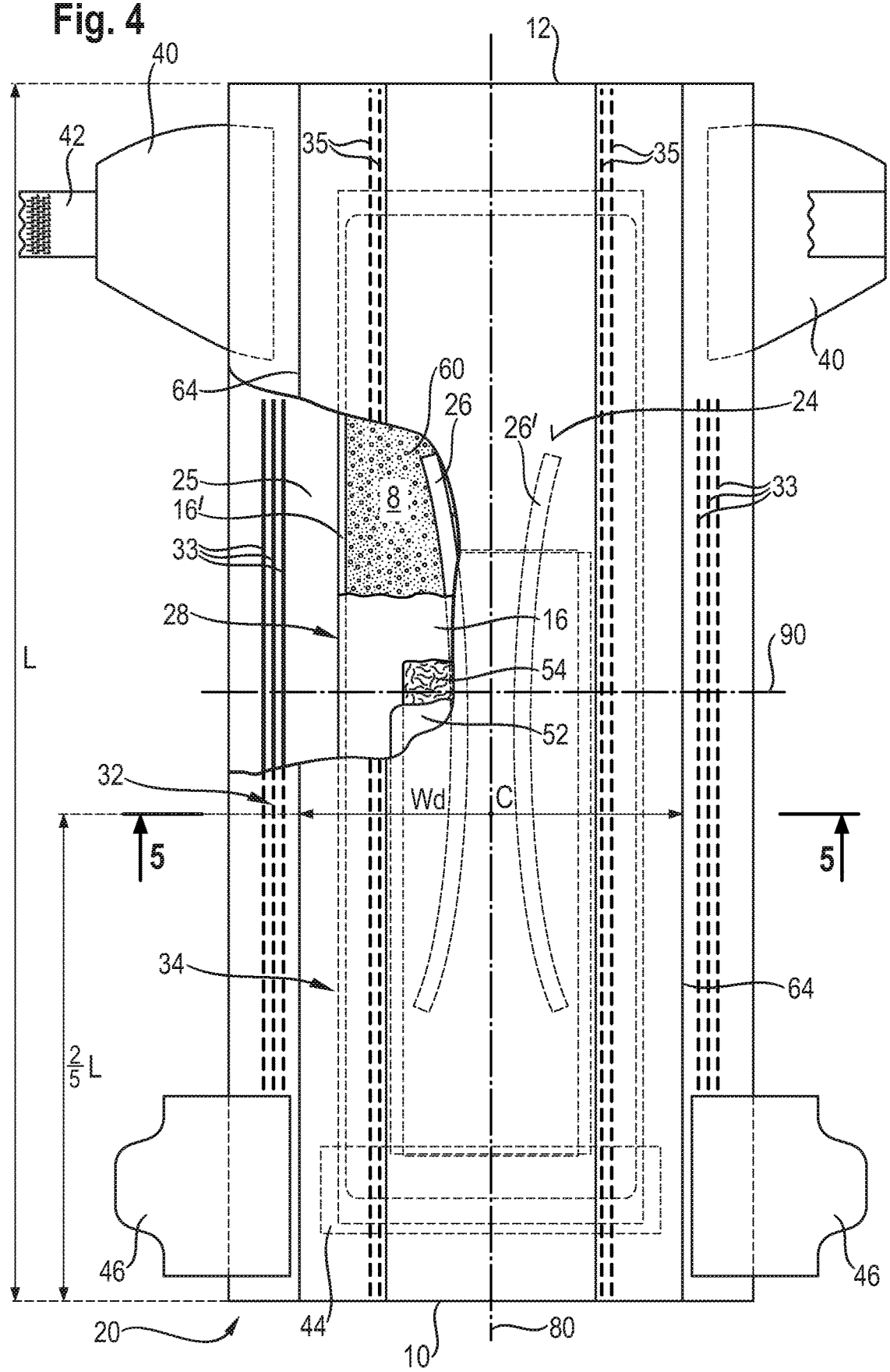
FIG. 4 is a top view of an alternative embodiment of the invention with two channels.
Figure 5:
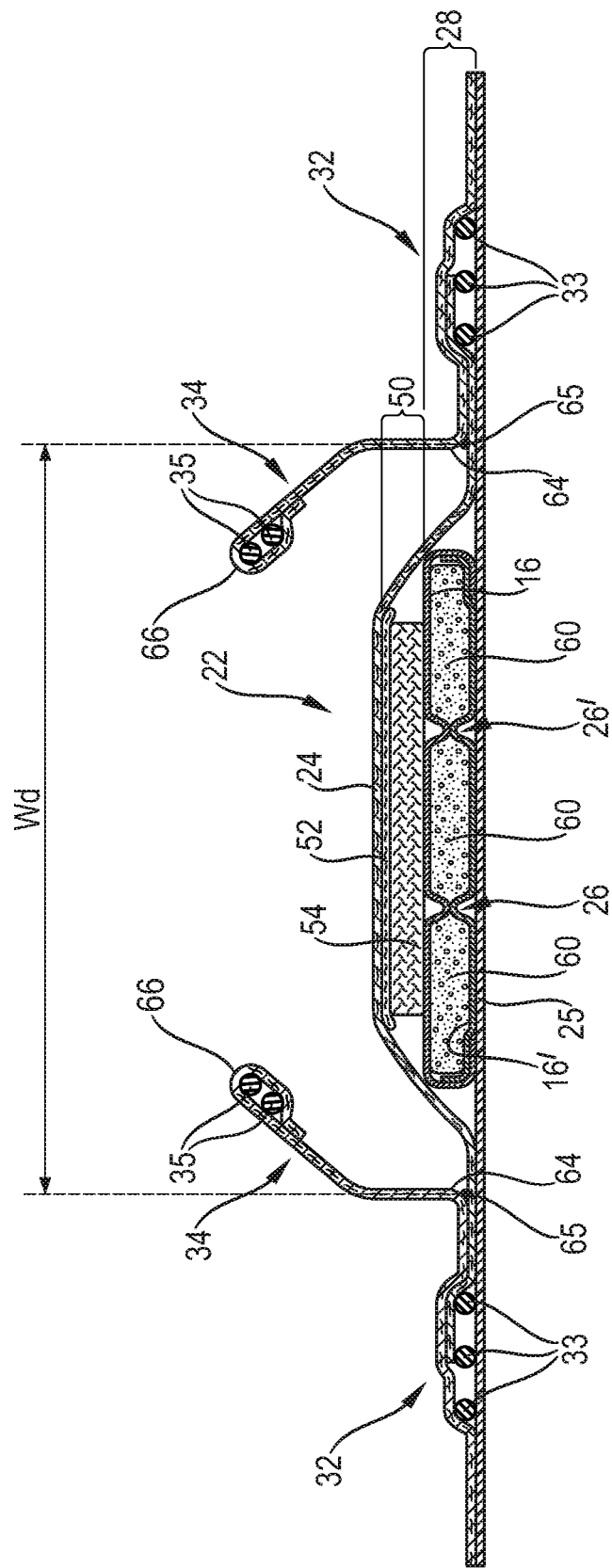
FIG. 5 is a transversal cross-section of the embodiment of FIG. 4 at the crotch point.
Figure 6:
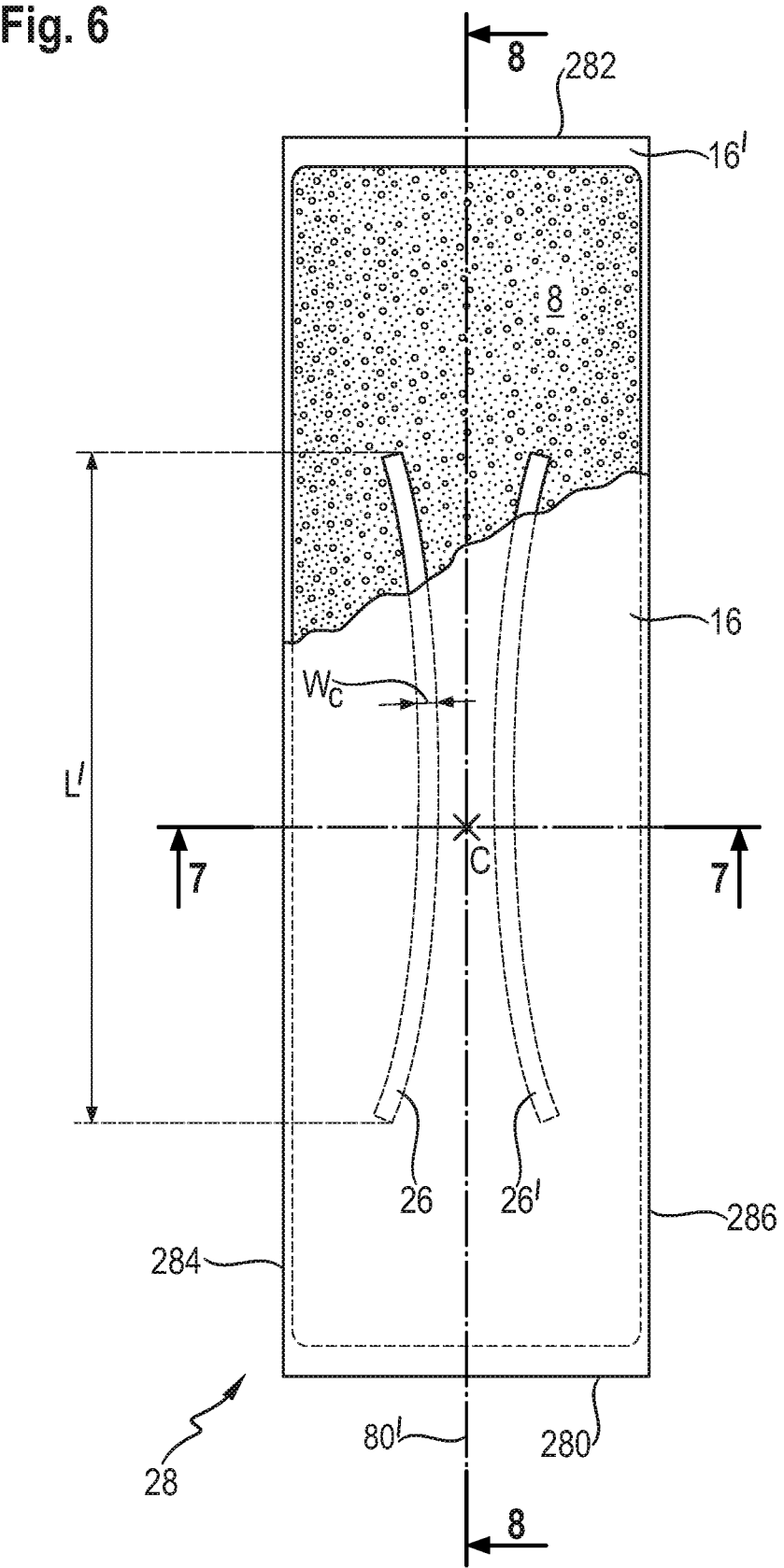
FIG. 6 is a top view of an embodiment of the absorbent core of FIG. 4 with some layers partially removed.
Figure 7:
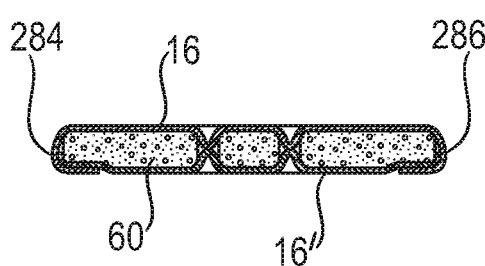
FIG. 7 is a transversal cross-section of the core of FIG. 6 at the crotch point.
Figure 8:
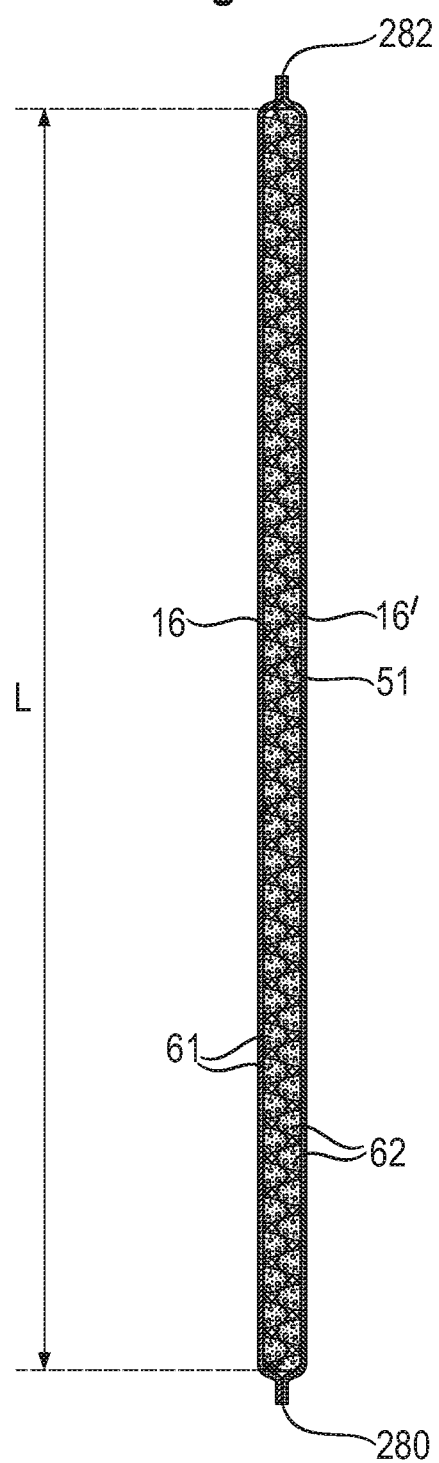
FIG. 8 is a longitudinal cross-section of the embodiment of FIG. 6.

The exemplary absorbent core 28 of the absorbent article of FIG. 4-5 is shown in isolation in FIGS. 6-8. The absorbent core typically comprises a front edge 280, a back edge 282 and two longitudinal edges 284, 286 joining the front edge 280 and the back edge 282. The absorbent core may also comprise a generally planar top edge and a generally planar bottom edge. The front edge 280 of the core is the edge of the core intended to be placed towards the front edge 10 of the absorbent article. The core may have a longitudinal axis 80' corresponding substantially to the longitudinal axis of the article 80, as seen from the top in a planar view as in FIG. 1. Typically the absorbent material will be advantageously distributed in higher amount towards the front edge than towards the back edge as more absorbency is required at the front. Typically the front and back edges of the core are shorter than the longitudinal edges of the core. The core wrap may be formed by two nonwoven material 16, 16' which may be at least partially sealed along the edges of the absorbent core. The core wrap may be at least partially sealed along its front edge, back edge and two longitudinal edges so that substantially no absorbent material leaks out of the absorbent core wrap.

The absorbent core of the invention may further comprise adhesive for example to help immobilizing the SAP within the core wrap and/or to ensure integrity of the core wrap, in particular when the core wrap is made of two or more substrates. The core wrap will typically extend to a larger area than strictly needed for containing the absorbent material within. The absorbent core advantageously achieve an SAP loss of no more than about 70%, 60%, 50%, 40%, 30%, 20%, 10% according to the Wet Immobilization Test described in WO2010/0051166A1.

Cores comprising relatively high amount of SAP with various core designs have been proposed in the past, see for example in U.S. Pat. No. 5,599,335 (Goldman), EP1,447,066 (Busam), WO95/11652 (Tanzer), US2008/0312622A1 (Hundorf), WO2012/052172 (Van Malderen).

The absorbent material may be a continuous layer present within the core wrap. In other embodiments, the absorbent material may be comprised of individual pockets or stripes of absorbent material enclosed within the core wrap. In the first case, the absorbent material may be for example obtained by the application of a single continuous layer of absorbent material. The continuous layer of absorbent material, in particular of SAP, may also be obtained by combining two absorbent layers having discontinuous absorbent material application pattern wherein the resulting layer is substantially continuously distributed across the absorbent particulate polymer material area, as taught in US2008/

0312622A1 (Hundorf) for example. The absorbent core 28 may for example comprise a first absorbent layer and a second absorbent layer, the first absorbent layer comprising a first substrate 16 and a first layer 61 of absorbent material, which may be 100% SAP, and the second absorbent layer comprising a second substrate 16' and a second layer 62 of absorbent material, which may also be 100% SAP, and a fibrous thermoplastic adhesive material 51 at least partially bonding each layer of absorbent material 61, 62 to its respective substrate. This is illustrated in FIG. 8 where the first and second SAP layers have been applied as transversal stripes or "land areas" having the same width as the desired absorbent material deposition area on their respective substrate before being combined. The stripes or land areas may be separated by junction areas. The stripes may advantageously comprise different amount of absorbent material (SAP) to provide a profiled basis weight along the longitudinal axis of the core 80'. The first substrate 16 and the second substrate 16' may form the core wrap.

The fibrous thermoplastic adhesive material 51 may be at least partially in contact with the absorbent material 61, 62 in the land areas and at least partially in contact with the substrate layer in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% SAP.

The thermoplastic adhesive material 51 may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

The thermoplastic polymer has typically a molecular weight (Mw) of more than 10,000 and a glass transition temperature (Tg) usually below room temperature or $-6°$ C.$<$Tg$<16°$ C. Typical concentrations of the polymer in a hotmelt are in the range of about 20 to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%.

The thermoplastic adhesive used for the fibrous layer preferably has elastomeric properties, such that the web formed by the fibers on the SAP layer is able to be stretched as the SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 issued to Korpman on Mar. 15, 1988.

The thermoplastic adhesive material is advantageously applied as fibers. The fibers may exemplarily have an average thickness of about 1 to about 50 micrometers or about 1 to about 35 micrometers and an average length of about 5 mm to about 50 mm or about 5 mm to about 30 mm. To improve the adhesion of the thermoplastic adhesive material to the substrate or to any other layer, in particular any other nonwoven layer, such layers may be pre-treated with an auxiliary adhesive. The fibers adhere to each other to form a fibrous layer, which can also be described as a mesh.

In certain embodiments, the thermoplastic adhesive material will meet at least one, or several, or all of the following parameters. An exemplary thermoplastic adhesive material may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more then 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

G' can be measured using a rheometer as indicated in WO2010/27719. The rheometer is capable of applying a shear stress to the adhesive and measuring the resulting strain (shear deformation) response at constant temperature. The adhesive is placed between a Peltier-element acting as lower, fixed plate and an upper plate with a radius R of e.g., 10 mm, which is connected to the drive shaft of a motor to generate the shear stress. The gap between both plates has a height H of e.g., 1500 micron. The Peltier-element enables temperature control of the material (+0.5° C.). The strain rate and frequency should be chosen such that all measurements are made in the linear viscoelastic region.

Superabsorbent Polymer (SAP)

"Superabsorbent polymers" ("SAP") as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). The SAP used may in particular have a CRC value of more than 20 g/g, or more than 24 g/g, or of from 20 to 50 g/g, or from 20 to 40 g/g, or 24 to 30 g/g. The SAP useful in the present invention include a variety of water-insoluble, but water-swellable polymers capable of absorbing large quantities of fluids.

The superabsorbent polymer can be in particulate form so as to be flowable in the dry state. Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in the PCT Patent Application WO07/047598 or for example WO07/046052 or for example WO2009/155265 and WO2009/155264. In some embodiments, suitable superabsorbent polymer particles may be obtained by current state of the art production processes as is more particularly as described in WO 2006/083584. The superabsorbent polymers are preferably internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as cross-linkers described in WO2009/155265. The superabsorbent polymer particles may be externally surface cross-linked, or: post cross-linked). Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP1,199,327 and morpholine-2,3-dione and its derivatives as described in WO03/031482.

In some embodiments, the SAP are formed from polyacrylic acid polymers/polyacrylate polymers, for example having a neutralization degree of from 60% to 90%, or about 75%, having for example sodium counter ions.

The SAP useful for the present invention may be of numerous shapes. The term "particles" refers to granules, fibers, flakes, spheres, powders, platelets and other shapes and forms known to persons skilled in the art of superabsorbent polymer particles. In some embodiments, the SAP particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 µm, and preferably less than 250 µm down to 50 µm. The length of the fibers is preferably about 3 mm to about 100 mm. The fibers can also be in the form of a long filament that can be woven.

Typically, SAP are spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, or from 50 to 850 µm, preferably from 100 to 710 µm, more preferably from 150 to 650 µm, as measured according to EDANA method WSP 220.2-05. SAP having a relatively low particle size help to increase the surface area of the absorbent material which is in contact with liquid exudates and therefore support fast absorption of liquid exudates.

The SAP may have a particle sizes in the range from 45 µm to 4000 µm, more specifically a particle size distribution within the range of from 45 µm to about 2000 µm, or from about 100 µm to about 1000, 850 or 600 µm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or preferably from 100 or 200 or 300 or 400 or 500 µm, or to 1000 or to 800 or to 700 µm; as can for example be measured by the method set out in for example EP-A-0,691,133. In some embodiments of the invention, the superabsorbent polymer material is in the form of particles whereof at least 80% by weight are particles of a size between 50 µm and 1200 µm and having a mass median particle size between any of the range combinations above. In addition, or in another embodiment of the invention, said particles are essentially spherical. In yet another or additional embodiment of the invention the superabsorbent polymer material has a relatively narrow range of particle sizes, e.g. with the majority (e.g. at least 80% or preferably at least 90% or even at least 95% by weight) of particles having a particle size between 50 µm and 1000 µm, preferably between 100 µm and 800 µm, and more preferably between 200 µm and 600 µm.

Suitable SAP may for example be obtained from inverse phase suspension polymerizations as described in U.S. Pat. Nos. 4,340,706 and 5,849,816 or from spray- or other gas-phase dispersion polymerizations as described in US Patent Applications No. 2009/0192035, 2009/0258994 and 2010/0068520. In some embodiments, suitable SAP may be obtained by current state of the art production processes as is more particularly described from page 12, line 23 to page 20, line 27 of WO 2006/083584.

The surface of the SAP may be coated, for example, with a cationic polymer. Preferred cationic polymers can include polyamine or polyimine materials. In some embodiments, the SAP may be coated with chitosan materials such as those disclosed in U.S. Pat. No. 7,537,832 B2. In some other embodiments, the SAP may comprise mixed-bed Ion-Exchange absorbent polymers such as those disclosed in WO 99/34841 and WO 99/34842.

The absorbent core will typically comprise only one type of SAP, but it is not excluded that a blend of SAPs may be used. The fluid permeability of a superabsorbent polymer can be quantified using its Urine Permeability Measurement (UPM) value, as measured in the test disclosed European patent application number EP12174117.7. The UPM of the SAP may for example be of at least $10 \times 10^{-7}$ cm$^3$·sec/g, or at least $30 \times 10^{-7}$ cm$^3$·sec/g, or at least $50 \times 10^{-7}$ cm$^3$·sec/g, or more, e.g. at least 80 or $100 \times 10^{-7}$ cm$^3$·sec/g. The flow characteristics can also be adjusted by varying the quantity and distribution of the SAP used in the second absorbent layer.

For most absorbent articles, the liquid discharge occurs predominately in the front half of the article, in particular for diaper. The front half of the article (as defined by the region between the front edge and a transversal line placed at a distance of half L from the front or back edge may therefore comprise most of the absorbent capacity of the core. Thus, at least 60% of the SAP, or at least 65%, 70%, 75% or 80% of the SAP may be present in the front half of the absorbent article, the remaining SAP being disposed in the back half of the absorbent article.

The total amount of SAP present in the absorbent core may also vary according to expected user. Diapers for newborns may require less SAP than infant or adult incontinence diapers. The amount of SAP in the core may be for example comprised from about 5 to 60 g, in particular from 5 to 50 g. The average SAP basis weight within the (or "at least one", if several are present) deposition area 8 of the SAP may be for example of at least 50, 100, 200, 300, 400, 500 or more g/m$^2$. The areas of the channels present in the absorbent material deposition area 8 are deduced from the absorbent material deposition area to calculate this average basis weight.

Core Wrap (16, 16')

The core wrap may be made of a single substrate folded around the absorbent material, or may advantageously comprise two (or more) substrates which are attached to another. Typical attachments are the so-called C-wrap and/or sandwich wrap. In a C-wrap, as exemplarily shown in FIGS. 2 and 7, the longitudinal and/or transversal edges of one of the substrate are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 or US2011/0250413A1. Nonwoven materials provided from synthetic fibers may be used, such as PE, PET and in particular PP.

If the core wrap comprises a first substrate 16 and a second substrate 16' these may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. It is advantageous that the top side of the core wrap, i.e. the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

Permanently hydrophilic nonwovens are also useful in some embodiments. Surface tension, as described in U.S. Pat. No. 7,744,576 (Busam et al.), can be used to measure how permanently a certain hydrophilicity level is achieved. Liquid strike through, as described in U.S. Pat. No. 7,744,576, can be used to measure the hydrophilicity level. The first and/or second substrate may in particular have a surface tension of at least 55, preferably at least 60 and most preferably at least 65 mN/m or higher when being wetted with saline solution. The substrate may also have a liquid strike through time of less than 5 s for a fifth gush of liquid. These values can be measured using the test methods described in U.S. Pat. No. 7,744,576B2: "Determination Of Surface Tension" and "Determination of Strike Through" respectively.

Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be said to be more hydrophilic than another.

The substrates may also be air-permeable. Films useful herein may therefore comprise micro-pores. The substrate may have for example an air-permeability of from 40 or from 50, to 300 or to 200 m$^3$/(m$^2$×min), as determined by EDANA method 140-1-99 (125 Pa, 38.3 cm$^2$). The material of the core wrap may alternatively have a lower air-permeability, e.g. being non-air-permeable, for example to facilitate handling on a moving surface comprising vacuum.

The core wrap may be at least partially sealed along all the sides of the absorbent core so that substantially no absorbent material leaks out of the core while performing the RCWR Test indicated below. By "substantially no absorbent material" it is meant that less than 5%, advantageously less than 2%, or less than 1% or 0% by weight of absorbent material escape the core wrap. In particular the core wrap should not in an appreciate way burst open while the test is conducted. The term "seal" is to be understood in a broad sense. The seal does not need to be continuous along the whole periphery of the core wrap but may be discontinuous along part or the whole of it, such as formed by a series of seal points spaced on a line. Typically a seal may be formed by gluing and/or thermal bonding.

If the core wrap is formed by two substrates 16, 16', four seals may be typically be used to enclose the absorbent material 60 within the core wrap. For example, a first substrate 16 may be placed on one side of the core (the top side as represented in the Figures) and extends around the core's longitudinal edges to at least partially wrap the opposed bottom side of the core. The second substrate 16' is typically present between the wrapped flaps of the first substrate 16 and the absorbent material 60. The flaps of the first substrate 16 may be glued to the second substrate 16' to provide a strong seal. This so called C-wrap construction can provide benefits such as improved resistance to bursting in a wet loaded state compared to a sandwich seal. The front side and back side of the core wrap may then also be sealed for example by gluing the first substrate and second substrate to another to provide complete encapsulation of the absorbent material across the whole of the periphery of the core. For the front side and back side of the core the first and second substrate may extend and be joined together in a substantially planar direction, forming for these edges a so-called sandwich construction. In the so-called sandwich construction, the first and second substrates may also extend outwardly on all sides of the core and be sealed flat along the whole or parts of the periphery of the core typically by gluing and/or heat/pressure bonding. Typically neither first nor second substrates need to be shaped, so that they can be rectangularly cut for ease of production but of course other shapes are possible.

The core wrap may also be formed by a single substrate which may enclose as in a parcel wrap the absorbent material and be for example sealed along the front side and back side of the core and one longitudinal seal.

Absorbent Material Deposition Area 8

The absorbent material deposition area 8 can be defined by the periphery of the layer formed by the absorbent material 60 within the core wrap, as seen from the top side of the absorbent core. The absorbent material deposition area 8 can take various shapes, in particular display a so-called "dog bone" or "hour-glass" shape, which shows a tapering along its width towards the middle or "crotch" region of the core. In this way, the absorbent material deposition area may have a relatively narrow width in an area of the core intended to be placed in the crotch region of the absorbent article, as illustrated in FIG. 1. This may provide for example better wearing comfort. The absorbent material deposition area 8 may thus have a width (as measured in the transversal direction) at its narrowest point which is less than about 100 mm, 90 mm, 80 mm, 70 mm, 60 mm or even less than about 50 mm. This narrowest width may further be for example at least 5 mm, or at least 10 mm, smaller than the width of the deposition area at its largest point in the front and/or back regions of the deposition area 8. The absorbent material deposition area 8 can also be generally rectangular, for example as shown in FIGS. 4-6, but other deposition areas can also be used such as a "T" or "Y" or "hour-glass" or "dog-bone" shape.

The basis weight (amount deposited per unit of surface) of the SAP may also be varied along the deposition area 8 to create a profiled distribution of absorbent material, in particular SAP, in the longitudinal direction, in the transversal direction, or both directions of the core. Hence along the longitudinal axis of the core, the basis weight of absorbent material may vary, as well as along the transversal axis, or any axis parallel to any of these axes. The basis weight of SAP in area of relatively high basis weight may thus be for example at least 10%, or 20%, or 30%, or 40%, or 50% higher than in an area of relatively low basis weight. In particular the SAP present in the absorbent material deposition area at the level of the crotch point C may have more SAP per unit of surface deposited as compared to another area of the absorbent material deposition area 8.

The absorbent material may be deposited using known techniques, which may allow relatively precise deposition of SAP at relatively high speed. In particular the SAP printing technology as disclosed for example in US2006/24433 (Blessing), US2008/0312617 and US2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate. The channels of the absorbent core can be formed for example by modifying the pattern of the grid and receiving drums so that no SAP is applied in certain areas to form absorbent material free areas in the form of channels. EP application number 11169396.6 discloses this modification in more details.

Channels 26, 26'

The absorbent material deposition area 8 comprises at least one channel 26, which is at least partially oriented in the longitudinal direction of the article 80. If the following the plural form "channels" will be used to mean "at least one channel". The channels may have a length L' projected on the longitudinal axis 80 of the article that is at least 10% of the length L of the article. The channels may be formed in various ways. For example the channels may be formed by zones within the absorbent material deposition area which may be substantially free of absorbent material, in particular SAP. In addition or alternatively, the channel(s) may also be formed by continuously or discontinuously bonding the top side of the core wrap to the bottom side of the core wrap through the absorbent material deposition area. The channels may be advantageously continuous but it is not excluded that the channels are intermittent. The acquisition-distribution system or any sub-layer between topsheet and absorbent core layer, or another layer of the article, may also comprise channels, which may or not correspond to the channels of the absorbent core.

The channels may in particular be present at least at the same longitudinal level as the crotch point C in the absorbent article, as represented in FIG. 1 with the two longitudinally extending channels 26, 26'. The channels may also extend from the crotch region or be present in the front region and/or in the back region of the article.

The absorbent core 28 may also comprise more than two channels, for example at least 3, or at least 4 or at least 5 or at least 6. Shorter channels may also be present, for example in the back region or the front region of the core as represented by the pair of channels 27, 27' in FIG. 1 towards the front of the article. The channels may comprise one or more pairs of channels symmetrically arranged relative to the longitudinal axis 80.

The channels may be particularly useful in the absorbent core when the absorbent material deposition area is rectangular, as the channels can improve the flexibility of the core to an extent that there is less advantage in using a non-rectangular (shaped) core. Of course channels may also be present in a layer of SAP having a shaped deposition area.

The channels may extend substantially longitudinally, which means typically that each channel extends more in the longitudinal direction than in the transverse direction, and typically at least twice as much in the longitudinal direction than in the transverse direction (as measured after projection on the respective axis). In some embodiments there is no completely or substantially transverse channels in the core.

The channels may be completely oriented longitudinally and parallel to the longitudinal axis but also may be curved. In particular some or all the channels, in particular the channels present in the crotch region, may be concave towards the longitudinal centerline 80, as for example represented in FIG. 1 for the pair of channels 26, 26'. The radius of curvature may typically be at least equal (and preferably at least 1.5 or at least 2.0 times this average transverse dimension) to the average transverse dimension of the absorbent layer; and also straight but under an angle of (e.g. from 5°) up to 30°, or for example up to 20°, or up to 10° with a line parallel to the longitudinal axis. The radius of curvature may be constant for a channel, or may vary along its length. This may also includes channels with an angle therein, provided said angle between two parts of a channel is at least 120°, preferably at least 150°; and in any of these cases, provided the longitudinal extension of the channel is more than the transverse extension. The channels may also be branched, for example a central channel superposed with the longitudinal axis in the crotch region which branches towards the back and/or towards the front of the article.

In some embodiments, there is no channel that coincides with the longitudinal axis 80 of the article or the core. When present as symmetrical pairs relative to the longitudinal axis, the channels may be spaced apart from one another over their whole longitudinal dimension. The smallest spacing distance may be for example at least 5 mm, or at least 10 mm, or at least 16 mm.

Furthermore, in order to reduce the risk of fluid leakages, the longitudinal main channels typically do not extend up to any of the edges of the absorbent material deposition area, and are therefore fully encompassed within the absorbent material deposition area of the core. Typically, the smallest distance between a channel and the closest edge of the absorbent material deposition area is at least 5 mm.

The channels may have a width Wc along at least part of its length which is at least 2 mm, or at least 3 mm or at least 4 mm, up to for example 20 mm, or 16 mm or 12 mm. The width of the channel may be constant through substantially the whole length of the channel or may vary along its length. When the channels are formed by absorbent material-free zone within the absorbent material deposition area, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels is the width of this bonding.

At least some or all the channels are advantageously permanent channels, meaning their integrity is at least partially maintained both in the dry state and in the wet state. Permanent channels may be obtained by provision of one or more adhesive material, for example the fibrous layer of adhesive material or a construction glue that helps adhering for example a substrate with an absorbent material within the walls of the channel. Permanent channels may be also in particular formed by bonding the upper side and lower side of the core wrap (e.g. first substrate 16 and the second substrate 16') together through the channels. Typically, an adhesive can be used to bond both sides of the core wrap through the channels, but it is possible to bond via other known means, such as pressure bonding, ultrasonic bonding or heat bonding or combination thereof. The core wrap can be continuously bonded or intermittently bonded along the channels. The channels may advantageously remain or become visible at least through the topsheet and/or backsheet when the absorbent article is fully loaded with a fluid as disclosed in the Wet Channel Integrity Test below. This may be obtained by making the channels substantially free of SAP, so they will not swell, and sufficiently large so that they will not close when wet. Furthermore bonding the core wrap to itself through the channels may be advantageous. The Wet Channel Integrity Test described below can be used to test if channels are permanent and visible following wet saturation and to what extent. Advantageously, a permanent channel according to the invention has a percentage of integrity of at least 20%, or 30%, or 40%, or 50%, or 60, or 70%, or 80%, or 90% following the Wet Channel Integrity Test.

Barrier Leg Cuffs 34

The absorbent article comprises a pair of barrier leg cuffs 34. The barrier leg cuffs can be formed from a piece of material, typically a nonwoven, which is partially bonded to the rest of the article so that a portion of the material, the barrier leg cuffs, can be partially raised away and stand up from the plane defined by the topsheet when the article is pulled flat as shown e.g. in FIG. 1. The barrier leg cuffs can provide improved containment of liquids and other body exudates approximately at the junction of the torso and legs of the wearer. The barrier leg cuffs extend at least partially between the front edge and the back edge of the diaper on opposite sides of the longitudinal axis and are at least present at the level of the crotch point (C). The barrier leg cuffs are delimited by a proximal edge 64 joined to the rest of the article, typically the topsheet and/or the backsheet, and a free terminal edge 66, which is intended to contact and form a seal with the wearer's skin. The barrier leg cuffs are joined at the proximal edge 64 with the chassis of the article by a bond 65 which may be made for example by gluing, fusion bonding or combination of known bonding means. The bond 65 at the proximal edge 64 may be continuous or intermittent. The side of the bond 65 closest to the raised section of the leg cuffs delimits the proximal edge 64 of the standing up section of the leg cuffs. The distance between the inner sides of these bonds 65 define the dry and wet width of the article at this level for the purpose of RCWR test (see below).

The barrier leg cuffs can be integral with the topsheet or the backsheet, or more typically be formed from a separate material joined to the rest of the article. Typically the material of the barrier leg cuffs may extend through the whole length of the diapers but is "tack bonded" to the topsheet towards the front edge and back edge of the article so that in these sections the barrier leg cuff material remains flush with the topsheet. Each barrier leg cuff 34 may comprise one, two or more elastic strings 35 close to this free terminal edge 66 to provide a better seal.

In addition to the barrier leg cuffs 34, the article may comprise gasketing cuffs 32, which are joined to the chassis of absorbent article, in particular the topsheet and/or the backsheet and are placed transversely outwardly relative to the barrier leg cuffs. The gasketing cuffs can provide a better seal around the thighs of the wearer. Usually each gasketing leg cuff will comprise one or more elastic string or elastic element comprised in the chassis of the diaper for example between the topsheet and backsheet in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier leg cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. All or a portion of the barrier leg and/or gasketing cuffs may be treated with a lotion.

Acquisition-Distribution System 50

The absorbent articles of the invention may comprise an acquisition-distribution layer or system 50 (herein "ADS"). The function of the ADS is to quickly acquire the fluid and distribute it to the absorbent core in an efficient manner The ADS may comprise one, two or more layers, which may form a unitary layer or remain discrete layers which may be attached to each other. In the examples below, the ADS comprises two layers: a distribution layer 54 and an acquisition layer 52 disposed between the absorbent core and the topsheet, but the invention is not restricted to this example.

Typically, the ADS will not comprise SAP as this may slow the acquisition and distribution of the fluid. The prior art discloses many type of acquisition-distribution system, see for example WO2000/59430 (Daley), WO95/10996 (Richards), U.S. Pat. No. 5,700,254 (McDowall), WO02/067809 (Graef). The ADS may comprise, although not necessarily, two layers: a distribution layer and an acquisition layer, which will now be exemplified in more details.

Distribution Layer 54

The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf. The cross-linked cellulosic fibers provide higher resilience and therefore higher resistance to the first absorbent layer against the compression in the product packaging or in use conditions, e.g. under baby weight. This provides the core with a higher void volume, permeability and liquid absorption, and hence reduced leakage and improved dryness.

Exemplary chemically cross-linked cellulosic fibers suitable for a distribution layer are disclosed in U.S. Pat. Nos. 5,549,791, 5,137,537, WO9534329 or US2007/118087. Exemplary cross-linking agents include polycarboxylic acids such as citric acid and/or polyacrylic acids such as acrylic acid and maleic acid copolymers. For example, the crosslinked cellulosic fibers may have between about 0.5 mole % and about 10.0 mole % of a C2-C9 polycarboxylic acid cross-linking agent, calculated on a cellulose anhydroglucose molar basis, reacted with said fibers in an intrafiber ester crosslink bond form. The C2-C9 polycarboxylic acid cross-linking agent may be selected from the group consisting of:

aliphatic and alicyclic C2-C9 polycarboxylic acids having at least three carboxyl groups per molecule; and
aliphatic and alicyclic C2-C9 polycarboxylic acids having two carboxyl groups per molecule and having a carbon-carbon double bond located alpha, beta to one or both of the carboxyl groups, wherein one carboxyl group in said C2-C9 polycarboxylic acid crosslinking agent is separated from a second carboxyl group by either two or three carbon atoms. The fibers may have in particular between about 1.5 mole % and about 6.0 mole % crosslinking agent, calculated on a cellulose anhydroglucose molar basis, reacted therewith in the form of intrafiber ester crosslink bonds. The cross-linking agent may be selected from the group consisting of citric acid, 1, 2, 3, 4 butane tetracarboxylic acid, and 1, 2, 3 propane tricarboxylic acid, in particular citric acid.

Polyacrylic acid cross-linking agents may also be selected from polyacrylic acid homopolymers, copolymers of acrylic acid, and mixtures thereof. The fibers may have between 1.0 weight % and 10.0 weight %, preferably between 3 weight % and 7 weight %, of these cross-linking agents, calculated on a dry fiber weight basis, reacted therewith in the form of intra-fiber crosslink bonds. The cross-linking agent may be a polyacrylic acid polymer having a molecular weight of from 500 to 40,000, preferably from 1,000 to 20,000. The polymeric polyacrylic acid cross-linking agent may be a copolymer of acrylic acid and maleic acid, in particular wherein the weight ratio of acrylic acid to maleic acid is from 10:1 to 1:1, preferably from 5:1 to 1.5:1. An effective amount of citric acid may be further mixed with said polymeric polyacrylic acid cross-linking agent.

The distribution layer comprising cross-linked cellulose fibers of the invention may comprise other fibers, but this layer may advantageously comprise at least 50%, or 60%, or 70%, or 80%, or 90% or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer 54 may be a material having a water retention value of from 25 to 60, preferably from 30 to 45, measured as indicated in the procedure disclosed in U.S. Pat. No. 5,137,537.

The distribution layer may typically have an average basis weight of from 30 to 400 g/m$^2$, in particular from 100 to 300 g/m$^2$. The density of the distribution layer may vary depending on the compression of the article, but may be of between 0.03 to 0.15 g/cm$^3$, in particular 0.08 to 0.10 g/cm$^3$ measured at 0.30 psi (2.07 kPa).

Acquisition Layer 52

The ADS may comprise an acquisition layer 52. The acquisition layer may be disposed between the distribution layer 54 and topsheet 24. The acquisition layer 52 may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round hollow PET staple fibers (50/50 or 40/60 mix of 6 denier and 9 denier fibers). An exemplary binder is a butadiene/styrene latex. Non-wovens have the advantage that they can be manufactured outside the converting line and stored and used as a roll of material.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co patent applications US2003/148684 to Cramer et al. and US2005/008839 to Cramer et al.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

Fastening System

The absorbent article may include a fastening system. The fastening system can be used to provide lateral tensions about the circumference of the absorbent article to hold the absorbent article on the wearer as is typical for taped diapers. This fastening system is not necessary for training pant article since the waist region of these articles is already bonded. The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached. Some exemplary surface fastening systems are disclosed in U.S. Pat. Nos. 3,848,594, 4,662,875, 4,846,815, 4,894,060, 4,946,527, 5,151,092 and 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,736, and 5,591,152.

Front and Back Ears 46, 40

The absorbent article may comprise front ears 46 and back ears 40 as is known in the art. The ears can be integral part of the chassis, for example formed from the topsheet and/or backsheet as side panel. Alternatively, as represented on FIG. 1, they may be separate elements attached by gluing and/or heat embossing or pressure bonding. The back ears 40 are advantageously stretchable to facilitate the attachment of the tabs 42 on the landing zone 40 and maintain the taped diapers in place around the wearer's waist. The back ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Relations Between the Layers

Typically, adjacent layers and components will be joined together using conventional bonding method such as adhesive coating via slot coating or spraying on the whole or part of the surface of the layer, or thermo-bonding, or pressure bonding or combinations thereof. This bonding is not represented in the Figures (except for the bonding between the raised element of the leg cuffs 65 with the topsheet 24) for clarity and readability but bonding between the layers of the article should be considered to be present unless specifically excluded. Adhesives may be typically used to improve the adhesion of the different layers, for example between the backsheet and the core wrap. The glue may be any standard hotmelt glue as known in the art.

If an acquisition layer 52 is present, it may be advantageous that this acquisition layer is larger than or least as large as the distribution layer 54 in the longitudinal and/or transversal dimension. In this way the distribution layer 52 can be deposited on the acquisition layer 54 during the manufacturing process before assembling these layers in the finished article. This simplifies handling, in particular if the acquisition layer is a nonwoven which can be unrolled from a roll of stock material. The distribution layer may also be deposited directly on the absorbent core's upper side of the core wrap or another layer of the article. Also, an acquisition layer 52 larger than the distribution layer allows to directly glue the acquisition layer to the storage core (at the larger areas). This can give increased integrity to the article and better liquid communication.

The absorbent core and in particular its absorbent material deposition area 8 may advantageously be at least as large and long and advantageously at least partially larger and/or longer than the acquisition-distribution system (ADS). This is because the absorbent material in the core can usually more effectively retain fluid and provide dryness benefits across a larger area than the ADS. The absorbent article may have a rectangular SAP layer and a non-rectangular (shaped) ADS. The absorbent article may also have a rectangular (non-shaped) ADS and a rectangular layer of SAP.

Method of Making the Article

The absorbent articles of the invention may be made by any conventional methods known in the art. In particular the articles may be hand-made or industrially produced at high speed.

Experimental Settings

The values indicated herein are measured according to the methods indicated herein below, unless specified otherwise. All measurements are performed at 21±2° C. and 50±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2-05.

Caliper Test

Equipment: Mitutoyo manual caliper gauge with a resolution of 0.01 mm—or equivalent instrument.

Contact Foot: Flat circular foot with a diameter of 17.0 mm (±0.2 mm) A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample. If there was a spring present to push the foot to the sample the spring is removed from the equipment, such that indeed the equipment applies a pressure of 2.07 kPa.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second

Sample Preparation:

If the absorbent articles are provided in a package, the sample articles to be tested are removed from the center area of a package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles. Care is taken to avoid touching and/or compressing the absorbent core and ADS area.

Measurement Procedure:

The article is laid flat on a counter top, garment-facing side down. A lateral line is drawn across the body-facing surface of the article at the level of the crotch point C.

The contact foot of the caliper gauge is raised and the article is placed on base plate, garment-facing surface side down so that when lowered, the center of the foot is on marked measuring point at the crotch point C.

The foot is gently lowered onto the article and released (ensure calibration to "0" prior to the start of the measurement). The caliper value is read to the nearest 0.01 mm, 10 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Wet Channel Integrity Test

This test is designed to check the integrity of a channel following wet saturation. The test can be performed directly on an absorbent article or on an absorbent core taken separately.

1. The full length (in millimeters) of the channel is measured in the dry state (if the channel is not straight, the curvilinear length through the middle of the channel is measured).

2. The absorbent article or core is then completely immersed in a large excess (e.g. 5 liters) of synthetic urine "Saline", with a concentration of 9.00 g NaCl per 1000 ml solution prepared by dissolving the appropriate amount of sodium chloride in distilled water. The temperature of the solution must be 20+/−5° C.

3. After 1 minute in the saline, the absorbent article or core is removed and held vertically by one end for 5 seconds to drain, then extended flat on an horizontal surface with the wearer (topsheet) side intended to be facing the wearer facing up. If the absorbent article or core comprises stretch elements, it is pulled taut in both X and Y dimensions so that no contraction is observed. The front and back edges of the absorbent article or core are fixed to an horizontal surface, so that no contraction can happen.

4. The absorbent article or core is covered with a rectangular suitably weighted rigid plate, with dimensions as follows: length equal to the full length of the absorbent article or core, and width equal to the maximum absorbent structure or core width at the widest point.

5. A pressure of 18.0 kPa is applied for 30 seconds over the area of the rigid plate above mentioned. Pressure is calculated on the basis of overall area encompassed by the rigid plate. Pressure is achieved by placing additional weights in the geometric center of the rigid plate, such that the combined weight of the rigid plate and the additional weights result in a pressure of 18.0 kPa over the total area of the rigid plate.

6. After 30 seconds, the additional weights and the rigid plate are removed.

7. Immediately afterwards, the cumulative length of the portions of the channel which remained intact is measured (in millimeters; if the channel is not straight, the curvilinear length through the middle of the channel is measured). If no portions of the channel remained intact then the channel is not permanent.

The percentage of integrity of the permanent channel is calculated by dividing the cumulative length of the portions of the channel which remained intact by the length of the channel in the dry state, and then multiplying the quotient by 100.

Relative Crotch Width Reduction (RCWR) Test

Principle: this test determines the amount of width reduction of the diaper at the level of crotch point following application of saline water according to the test protocol below. The crotch point is the point on the longitudinal axis placed at a distance of two fifth (⅖), as measured from the front edge, of the length L of the article.

The distance between the proximal ends 64 of the standing sections 34 of the raised leg cuffs at the level of the crotch point C of the absorbent article defines the crotch width of the article. The method requires separately measuring the dry crotch width Wd (i.e. before use) and the wet crotch width Ww (of the loaded absorbent article).

Sample preparation: the dry weight of the article is measured and recorded as Md. The absorbent article is placed with the topsheet side up on a sufficiently large Plexiglas plate. The front and rear edges of the absorbent article are fixed with clamps on the Plexiglas plate such that the article lays flat on the plate. The clamps are applied only in the front and the back regions of the absorbent article and should apply enough tension to flatten the article. For a pants type of absorbent article, the absorbent article is cut open at the side seams. If the pants type absorbent article does not have side seams it is cut at the corresponding two side positions at the belt. For absorbent articles that come with a fastening system the article is opened. The Plexiglas plate together with the absorbent article is placed in horizontal position with the topsheet of the article facing upwards.

The longitudinal axis is marked on the topsheet of the absorbent article and the length of the article L between front and back edge is measured. The longitudinal axis generally divides the product along its length into two roughly symmetric pieces in the plane of the topsheet. The crotch line is also marked on the topsheet. The crotch line is perpendicular to the longitudinal axis in the plane of the topsheet, crosses the longitudinal axis at ⅖ of the absorbent articles length L, measured from the front edge of the absorbent article. The front is the part of the absorbent article intended to be placed closer to the belly button of the wearer. The back is the part closer to the buttocks.

Measuring the Dry Crotch Width Wd:

As indicated before, the barrier leg cuffs 34 is the portion of the cuffs which can be raised away from the plane defined by the topsheet. The barrier leg cuffs 34 are bonded to the rest of article, typically the topsheet, at their proximal edges 64 by one or more bond 65. The dry crotch width Wd is determined by measuring with a caliper gauge the distance along the crotch line from the innermost bond 65 of one barrier leg cuff to the innermost bond 65 of the opposed barrier leg cuff, as represented in FIGS. 2-3. The barrier leg cuffs can be gently held outwardly of the article for the measurement of the dry and wet width, so that the measuring gauge can be held directly at the side of the bond closest to the longitudinal axis. The tips of the caliper gauge should touch the two intersections of the crotch line and the proximal edge of the barrier leg cuff. The tips of the caliper gauge should touch, but not distort the intersections. The caliper gauge should not touch other part(s) of the absorbent article. The dry crotch width is recorded as Wd. The dry crotch width (Wd) of the article of the invention range from to 70 mm to 200 mm.

Absorbent article loading: The fluid loading step is used to load the absorbent article in a reproducible manner A sufficiently large bowl with a large excess amount of saline solution (0.9% NaCl) is provided on a flat support. The absorbent article still attached to the Plexiglas plate is loaded by fully immersing it into the bowl with saline with the Topsheet side up into the bowl so that the liquid is covering the entire absorbent article for 15 seconds. The saline needs to fully cover the surface of the absorbent article during the entire time. The Plexiglas plate (with the absorbent article) is removed from the bowl immediately after the 15 seconds. The absorbent article is let to equilibrate for minutes by placing the Plexiglas plate in horizontal position with the article facing up.

Wet measurement: After these 3 minutes, the wet crotch width is measured and reported as Ww. The wet crotch width is measured by applying the caliper gauge at the crotch line and measuring the distance between the two proximal edges of the barrier leg cuffs without wrinkling the absorbent material in the same manner as was measured the dry width Wd. The absorbent article is then removed from the Plexiglas plate and the wet weight of the absorbent article is measured. This is recorded as the wet weight Mw.

Calculation of the Relative Crotch Width Reduction (RCWR):

The RCWR is calculated according to the following formula:

$$RCWR = \frac{Wd - Ww}{Mw - Md}$$

EXPERIMENTAL

The following products according to the invention were prepared:

Invention Example 1

Diapers having a rectangular absorbent material deposition area and two pair of channels similar to one represented for embodiment of FIG. 1 were prepared with the following specification. One pair of channel was relatively long and mainly present in the crotch region of the article and the other pair was smaller and placed towards the front of the article. The channels were absorbent material free and the top and bottom sides of the core wrap were attached together through these channels. The width of the channels was uniformly 8 mm and the projected lengths on the longitudinal axis of the article of the long and short channels were about 170 mm and 40 mm respectively. The longer channels were curved and concave towards the longitudinal centerline of the article as shown in FIG. 1. The smallest distance between the longer channels was about 16 mm. The smallest distance between the shorter channels was about 14 mm. The smaller channels were also slightly curved.

The absorbent core comprised in total 14.1 g fast absorbing SAP applied in an area of deposition having a length of 360 mm and a shaped width profile as shown in FIG. 1. The width of the absorbent material deposition area was 110 mm at the front and the back of the deposition area and 90 mm at the crotch point of the absorbent material deposition area. The SAP was distributed so that the basis weight of SAP was higher in the crotch region than at the front region and still lower towards the back region. There was no profiling of the SAP in the transversal direction ("cross-machine direction" or "CD"). The absorbent core was formed by SAP printing technology as disclosed in US2010/0051166A1, which combines two nonwoven substrates each supporting a SAP layer and having a microfiber elastic glue applied on each SAP layer which immobilizes the SAP layer on the substrate. These nonwoven substrates form the core wrap by C-wrapping to upper substrate onto the lower substrate. Auxiliary glue was applied between the SAP layers and their respective substrate which was slot coated with 41 slots 1 mm wide with a distance of 1 mm between the slots along the whole length of the core wrap (390 mm). The microfiber glue (from H. B. Fuller) applied on each SAP layer was uniformly applied at width of 108 mm and length of 390 mm on each SAP layer, 0.211 g of microfiber glue was used on the core cover (top) side and 0.168 g on the dusting layer (bottom) side. The channels were formed by using a suitable printing drum delimiting the channels shape, further information on how to form channels can be found in EP application number EP12174117.7 using printed SAP technology.

The core wrap had a length of 390 mm with two end flaps free of absorbent material having a length of 15 mm at the back and at the front of the absorbent core. The front and back end seals of the core were slot glued together, the glue slots having a length of 30 mm from the front end seal and 20 mm from the back end seal. The folded width of the core wrap was 120 mm. The core wrap comprised two nonwovens, the top substrate (16 in FIG. 1, referred further as "Core cover") was a 10 gsm SMMS nonwoven treated by a surfactant to be hydrophilic. The lower substrate (16' in FIG. 1, referred further as "Dusting layer") was a 11 gsm SMMS nonwoven. The core cover was cut at a length of 390 mm and a cut width of 165 mm. The dusting layer had a cut length of 390 mm and a cut width of 130 mm. The core cover was C-wrapped around the dusting layer on the lateral sides of the core and the lateral edges of the dusting layer slightly formed upwards on the edge of the absorbent material of the core so that the overall width of the folded core wrap was about 120 mm.

The core cover and dusting layer were bonded together through the channels. The bond was formed by the auxiliary and microfiber glue discussed hereinabove. The bond was strong.

The acquisition-distribution system was formed by an acquisition layer of 43 gsm latex bonded nonwoven having a length of 298 mm and a width of 90 mm, and a distribution layer of cross-linked cellulose fibers having a length of 248 mm and a width of 80 mm with a uniform basis weight of 207 gsm. The acquisition layer was glued to the distribution layer and the distribution layer was glued to nonwoven core cover using slot coating. The topsheet was a 15 gsm nonwoven and the backsheet a 16 gsm impermeable film.

The leg cuffs were commercial leg cuffs similar to those shown in FIG. 1-2, and comprised two 15 gsm, 478 mm long and 77 mm wide nonwovens on each side of the diaper. The leg cuffs were tackdown bonded at a distance of 100 mm from the front and 91 mm from the back of the edges of the diaper at a distance of 4 mm from the free edge. The nonwovens were fusion bonded along their length to the topsheet with a continuous bond width of 3 mm along their bond line. A 1 mm wide slot of glue was further applied along the continuous bond between the leg cuff material and the topsheet. The distance between the continuous bonds was 148 mm (this distance corresponding to Wd). The gasketing cuffs (the part of the cuffs not raised) were elasticized with three lines of elastic adhesive (ref. 33 in the Figures) on each side of the cuffs, starting at 75 mm from the front edge of the diaper and extending along a length of 266 mm for the two outmost lines and 301 mm for the innermost line. The raised barrier leg cuffs were elasticized with two elastics (ref. 35 in the Figs.) each close to the terminal edge (ref. 66 in the Figs.) of the barrier leg cuffs. These elastic had a pre strain of 300% and a contracted cut length of 119.5 mm. The glued in elastic length was 298 mm. The various components of the diapers were assembled in a conventional manner, typically by gluing or fusion bonding, unless indicated otherwise.

Invention Example 2

The diapers made for the second example were similar to these of Invention example 1. The core comprised two pair of channels, one relatively long in the crotch portion and one relatively smaller towards the front of the article. The channels were as in example 1 material free and the core wrap was attached to itself through the channels. The same materials were used in all invention examples unless otherwise indicated.

The differences with example 1 included a SAP distribution area which was rectangular with a width of 110 mm and a length of 360 mm. The acquisition layer was 318 mm long and 90 mm wide. The distribution layer was profiled in the longitudinal direction, having a higher basis towards the front and crotch region than in the back region of the diaper. The basis weight of the distribution layer was 196.5 gsm for the first 247 mm from the front and 120 gsm from the back 41 mm with a 10 mm transition length for a total length of 298 mm and a width of 80 mm. There was no auxiliary glue on the core cover side. The basis weight of the glue for the front and back core wrap end seals was 15 gsm instead of 20 gsm for invention example 1.

Invention Example 3

This example was made in the same way as example 1 with the difference that the absorbent material (SAP) distribution area was rectangular with a SAP deposition width of 110 mm and comprised only one pair of absorbent material free channels in the crotch region of the absorbent article, as exemplarily shown in FIGS. 4 and 5. The channels were symmetric in relation to the longitudinal axis 80 had a projected length thereon of about 227 mm, a width of about 8 mm and a shortest distance from each other of 20 mm. Another difference with example was that there was no auxiliary glue between the SAP layer and the substrate on the dusting layer, and the dusting layer was a 10 gsm nonwoven. The distribution layer was 298 mm long and 80 mm wide with an homogenous basis weight of 176 gsm. As for the previous examples, the core cover was C-wrapped around the dusting layer and both layer permanently bonded through the channels.

Prior Products

Several commercially available products were also tested, all in size 4 unless indicated otherwise:

Example 4 was a commercially available in Germany Pampers® Baby-Dry diaper. The absorbent core in this product is made of a mixture of cellulose fluff and SAP. This product comprises a dual layer acquisition-distribution system similar to the one used in the invention examples.

Example 5 was a German commercially available Pampers® Active Fit diaper. The absorbent core in this product does not comprise cellulose fluff, the absorbent material comprises essentially SAP. This product also comprises a dual layer acquisition-distribution system similar to the one used in the invention examples.

Example 6 was a diaper commercially available in Sweden under the tradename Libero® manufactured by SCA. The diaper comprises a cellulose fluff/SAP mixed core featuring two material free channels in the crotch region of the core.

Example 7 was a diaper commercially available in Germany at the retailer Lidl® under the Tradename Toujours. The absorbent core of this product is essentially cellulose fluff free. While not being wished to be bound by theory, it is believed that this product is made according to the teaching of WO 2012/048879 (Van De Maele).

Example 8 was an adult incontinence pant product in size M commercially available in Japan from the company Unicharm. This product has a cellulose-free absorbent core comprising relatively large pockets of SAP separated by transversally extending glue bonds. While not wishing to be bound by this assessment, the structure seems similar to the ones described in Unicharm WO2012/101934 A1 and WO2012/102034 A1.

Test Results

For five samples of each above mentioned products, width reduction and load were measured as indicated in the Test method described above to determine the RCWR of the products. The averaged results are compiled below:

|  | Width Reduction (mm) | Load (g) | RCWR (mm/kg) |
|---|---|---|---|
| Invention Example 1 (4 channels, shaped absorbent material deposition area) | 11.8 | 233 | 50.9 |
| Invention Example 2 (4 channels, rectangular absorbent material deposition area) | 10.0 | 396 | 32.6 |
| Invention Example 3 (2 channels, rectangular absorbent material deposition area) | 9.0 | 213 | 42.7 |
| Example 4 (Pampers ® Baby-Dry) | 7.9 | 427 | 25.1 |
| Example 5 (Pampers ® Active Fit) | 5.8 | 236 | 24.6 |
| Example 6 Libero ® | 8.3 | 417 | 19.8 |
| Example 7 Toujours ® Diapers from Lidl ® | 5.0 | 218 | 22.9 |
| Example 8 Adult Pant from Unicharm | 6.6 | 234 | 27.9 |

Discussion

While not wishing to be bound by theory it is believed that the following features can provide alone or in combinations an increase in the RCWR relative to an absorbent article missing one or more of the below features. None of these features should be considered as being limited the scope of the claims unless specifically claimed.
1) The top side of the core wrap, which contacts the upper side of the absorbent material, and the bottom portion of the core wrap, which contacts the lower side of the absorbent material, may advantageously be at least partially bonded to each other through the channels. These bonds may be continuous or intermittent, and may be made via gluing and/or heat bonding, and may advantageously be sufficiently strong to resist delamination upon fluid loading ("permanent channels"), as discussed above. By constraining the core wrap in the channels, these bonds increase the strain of the core wrap and can promote core width reduction upon loading.
2) The core wrap may comprise a first layer and a second layer, both typically made of a nonwoven, wherein the first layer forms a C-wrap around the second layer at least along the longitudinal edges of the core. The first layer may be the layer forming the top side of the core wrap and the second layer may be the layer forming the bottom side of the core wrap. Typically the layers are bonded, for example by gluing, along the wrapped flaps of the first layer together with the bottom side of the second layer. The inventors believe that a C-wrap, especially along part or whole of the longitudinal sides of the absorbent material, can better restrain the absorbent material from expanding towards the sides of the article, thus providing for more expansion of the absorbent material in the vertical direction and providing for increasing contraction of the width of the article at the crotch point as the layers of the absorbent article contracts to follow this expansion.
3) Relatively inelastic materials can be used for the core wrap, as these will provide more constrain than relatively more elastic material and thus will follow the vertical (thickness direction) expansion of the absorbent material by reducing the width of the absorbent core.
4) A higher relative amount of SAP material in the core absorbent material will provide a relatively larger expansion of the core upon loading than a core comprising higher amount of non superabsorbent absorbent material such as cellulose fluffs. It may also be advantageous to have a higher basis weight of SAP in the crotch region of the article.
5) The core can be directly or indirectly joined to the backsheet to provide a larger reduction of the article width, as the backsheet will follow the contraction of the core as the core is loaded.

The above listed factors were identified by the inventors as potential features that may be used alone or in combination to increase the RCWR of an absorbent article. They should not be seen as limiting the scope of the claims, unless expressly mentioned in the claims, but may serve as guidelines for the skilled person to design an absorbent article providing the RCWR claimed. The Relative Crotch Width Reduction at the crotch point may advantageously ranges from 32 mm/kg to 150 mm/kg, in particular from 35 mm/kg to 100 mm/kg.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. An absorbent article comprising a front region, a back region, a crotch region disposed between the front region and the back region, and a longitudinal axis extending in a longitudinal direction of the article, the absorbent article comprising:
   a) a liquid permeable topsheet comprising a plurality of apertures and embossing;

b) a liquid impermeable backsheet;

c) an absorbent core disposed between the topsheet and backsheet, the absorbent core comprising a combination of superabsorbent polymer and cellulose fibers;

d) an acquisition-distribution layer disposed between the absorbent core and the topsheet, wherein the acquisition-distribution layer is devoid of superabsorbent polymer and channels;

e) at least one channel positioned within a layer located between the topsheet and the backsheet and having a longitudinally-extending length, wherein the at least one channel is disposed within the crotch region, and wherein the at least one channel is substantially free of fibers and superabsorbent polymer; and f) a pair of elastically extensible back ears;

wherein an indentation occurs in the backsheet that correspond to the at least one channel when the article is loaded with fluid.

2. The absorbent article of claim 1, further comprising an elastic waist feature disposed in the back region of the absorbent article and extending longitudinally outward from a waist edge of the absorbent core.

3. The absorbent article of claim 1, wherein the at least one channel has a width that varies along its length.

4. The absorbent article of claim 1, wherein the at least one channel has a width from 2 mm to 20 mm.

5. The absorbent article of claim 1, wherein the acquisition-distribution layer comprises a nonwoven.

6. The absorbent article of claim 1, comprising two channels.

7. The absorbent article of claim 6, wherein the two channels are symmetrically arranged relative to the longitudinal axis.

8. The absorbent article of claim 1, wherein the article has a Relative Crotch Width Reduction (RCWR) of 32-150 mm/kg, wherein the RCWR is calculated according to the formula:

$$RCWR = \frac{Wd - Ww}{Mw - Md}$$

wherein Wd is the dry crotch width, wherein Ww is the wet crotch width at the crotch point, wherein Mw is the wet mass of the article, wherein Md is the dry mass of the article, wherein the measurements are made as indicated according to the RCWR Test.

9. The absorbent article of claim 8, wherein the article has a dry crotch width Wd of from about 70 mm to about 200 mm.

10. The absorbent article of claim 1, further comprising a primary fastening system comprising a pair of primary fasteners, wherein each of the primary fastener of the pair of primary fasteners is joined to a back ear of the pair of elastically extensible back ears.

11. The absorbent article of claim 10, further comprising a secondary fastening system comprising a pair of secondary fasteners disposed in the front region of the absorbent article.

12. The absorbent article of claim 1, further comprising leg cuffs.

13. The absorbent article of claim 12, wherein each leg cuff of the pair of leg cuffs if formed from a single piece of material.

14. The absorbent article of claim 1, further comprising an elastic waist feature disposed in the front region of the absorbent article.

15. The absorbent article of claim 14, wherein the elastic waist feature extends longitudinally outward from a waist edge of the absorbent core.

16. An absorbent article comprising a front region, a back region, a crotch region disposed between the front region and the back region, and a longitudinal axis extending in a longitudinal direction of the article, the absorbent article comprising:

a) a liquid permeable topsheet comprising a plurality of apertures and embossing, wherein the embossing is disposed only on a portion of the topsheet;

b) a liquid impermeable backsheet;

c) an absorbent core disposed between the topsheet and backsheet, the absorbent core comprising a combination of superabsorbent polymer and cellulose fibers;

d) an acquisition-distribution layer disposed between the absorbent core and the topsheet, wherein the acquisition-distribution layer is devoid of superabsorbent polymer and channels;

e) a pair of channels positioned within a layer located between the topsheet and the backsheet and having a longitudinally-extending length, wherein the pair of channels are disposed within the crotch region, wherein the pair of channels are substantially free of fibers and superabsorbent polymer, and wherein the channels are symmetrically arranged relative to the longitudinal axis; and f) a pair of elastically extensible back ears;

wherein an indentation occurs in the backsheet that correspond to the channels when the article is loaded with fluid.

17. The absorbent article of claim 16, further comprising an elastic waist feature disposed in the back region of the absorbent article and extending longitudinally outward from a waist edge of the absorbent core.

18. The absorbent article of claim 16, wherein each channel of the pair of channels has a width that varies along its length.

19. An absorbent article comprising a front region, a back region, a crotch region disposed between the front region and the back region, and a longitudinal axis extending in a longitudinal direction of the article, the absorbent article comprising:

a) a liquid permeable topsheet comprising:
   a plurality of apertures comprising a primary aperture, wherein the primary aperture differs from the remainder of the plurality of apertures in size, and embossing;

b) a liquid impermeable backsheet;

c) an absorbent core disposed between the topsheet and backsheet, the absorbent core comprising a combination of superabsorbent polymer and cellulose fibers;

d) an acquisition-distribution layer disposed between the absorbent core and the topsheet, wherein the acquisition-distribution layer is devoid of superabsorbent polymer and channels;

e) at least one channel positioned within a layer located between the topsheet and the backsheet and having a longitudinally-extending length, wherein the at least one channel is disposed within the crotch region, and wherein the at least one channel is substantially free of fibers and superabsorbent polymer; and f) a pair of elastically extensible back ears;

wherein an indentation occurs in the backsheet that correspond to the at least one channel when the article is loaded with fluid.

* * * * *